United States Patent
Kabakov

(10) Patent No.: US 8,439,842 B2
(45) Date of Patent: May 14, 2013

(54) METHOD AND DEVICE FOR CONTROLLING TRANSMISSION POWER OF AN ACTIVE TRANSDUCER

(75) Inventor: Serguei Kabakov, Laurel, MD (US)

(73) Assignee: General Electric Company, Schenectady, NY (US)

(*) Notice: Subject to any disclaimer, the term of this patent is extended or adjusted under 35 U.S.C. 154(b) by 811 days.

(21) Appl. No.: 12/361,901

(22) Filed: Jan. 29, 2009

(65) Prior Publication Data

US 2010/0191117 A1  Jul. 29, 2010

(51) Int. Cl.
*A61B 8/02* (2006.01)

(52) U.S. Cl.
USPC .......................... 600/453; 600/437

(58) Field of Classification Search .......... 600/437, 600/453–457
See application file for complete search history.

(56) References Cited

U.S. PATENT DOCUMENTS

| | | | |
|---|---|---|---|
| 3,982,528 A | 9/1976 | Phillipps | |
| 3,991,365 A | 11/1976 | Takeuchi | |
| 4,519,396 A | 5/1985 | Epstein et al. | |
| 4,569,356 A | 2/1986 | Kyozuka | |
| 4,573,479 A | 3/1986 | Tuccillo | |
| 4,641,657 A | 2/1987 | Ellis | |
| 5,123,420 A | 6/1992 | Paret | |
| 5,170,791 A | 12/1992 | Boos et al. | |
| 5,584,295 A * | 12/1996 | Muller et al. | 600/300 |
| 5,827,969 A * | 10/1998 | Lee et al. | 73/627 |
| 5,924,980 A | 7/1999 | Coetzee | |
| 2005/0251044 A1* | 11/2005 | Hoctor et al. | 600/444 |
| 2007/0189455 A1* | 8/2007 | Allison | 378/95 |

FOREIGN PATENT DOCUMENTS

| | | |
|---|---|---|
| DE | 103 45 717 A1 | 4/2005 |
| WO | 97/47242 A1 | 12/1997 |
| WO | 03/092490 A2 | 11/2003 |

OTHER PUBLICATIONS

Boos, Andreas et al; A New, Lightweight Fetal Telemetry System; Hewlett-Packard Juornal; Dec. 1995; pp. 82-93.
Je_Ewski, Janusz; Monitoring of mechanical and electrical activity of fetal heart: Determination of the FHR; Archives of Perinatal Medicine 8(1), 2002; pp. 33-39. [Abstract].
Lee, J.H. et al; Fast cross-correlation method for real time detection of fetalheart rate; Engineering in Medicine and Biology Society, 1998, Proceedings of the 20th Annual International Conference of the IEEE; vol. 1, Issued Oct. 29-Nov. 1, 1998; pp. 178-181. [Abstract].

(Continued)

*Primary Examiner* — Long V. Le
*Assistant Examiner* — Farshad Negarestan
(74) *Attorney, Agent, or Firm* — Andrus, Sceales, Starkes & Sawall, LLP

(57) ABSTRACT

A method of operating an ultrasound signal generator includes generating a stimulus signal and receiving a returned signal. The Signal to Noise Ratio (SNR) of the returned signal is computed. The SNR is compared to an optimal SNR range. A control signal is generated to control the transmission power of the stimulus signal. A new stimulus signal is generated at the new transmission power. A device for collecting and analyzing a quasi-periodic signal includes a SNR calculator that computes the SNR of a returned signal. A signal analysis selector selects between a first and a second signal analysis technique. A transmission power controller compares the computed SNR with an optimal SNR range for the selected technique and modifies the transmission power as a result of this comparison.

18 Claims, 18 Drawing Sheets

OTHER PUBLICATIONS

Pretlow, Robert A. III et al; Signal Processing Methodologies for an Acoustic Fetal Heart Rate Monitor; Sep. 1992; Department of Electrical & Computer Engineering College of Engineering & Technology, Old Dominion University; Norfolk, VA 23529; (see pp. 23-25).

Schlindwein, Fernando S. et al; Noninvasive Determination of Fetal Heart Rate and Short Term Heart Rate Variability Using Solely Doppler Ultrasound With Autocorrelation.

Smith, J.H. et al; Improvements in the registration and analysis of fetal heart rate records at the bedside; Obstet Gynaecol.; Apr. 1985; 92 (4); pp. 317-325. [Abstract].

Spencer, J.A.; Current methods of continuous fetal heart rate monitoring; Prof. Nurse, Dec. 1992 ; 8(3); pp. 173-175. [Abstract].

Tuck, D.L. et al; Improvement in Doppler ultrasound human foetal heart rate records by signal correlation; Medical & Biological Engineering & Computing, May 1982; vol. 20; pp. 357-360. [Abstract].

Hua, Xiao et al; A new algorithm for detecting fetal heart rate using ultrasound Doppler signals; Ultrasonics, vol. 43, Issue 6, May 2005, pp. 399-403. [Abstract].

Xiong, Xianming et al; DSP-based Design of Ultrasound Doppler Fetal Heart Rate Monitor; Guilin University of Electronic Technology. [Abstract].

Yamakoshi, Yoshiki et al; Fetal Heart Rate Estimation by an Ultrasonic Wave Direct Digital Detection and Complex Auto Correlation; Transactions of the Institute of Electronics; 2001; vol. J84; No. 12, pp. 1414-1420. [Abstract].

Zhang, C. et al; An improved auto-correlation method for Doppler fetal heart rate measurement. [Abstract}.

Zhi-Lin, Zhang et al; A Two-Stage Based Approach for Extracting Periodic Signals; ICA 2006; LNCS 3889; 2006; pp. 303-310.

Kulik et al., "Herzfrequenzermittlung Aus Dem Ultraschall-Dopplersignal Im Fetalmonitor FMT 2000, Teil 1: Verfahrensgrundlagen", Medizintechnik, Kunst und Wissen Erich Beiber, vol. 30, No. 2, Jan. 1, 1990, pp. 33-35 XP000214493.

European Search Report dated Jun. 7, 2010.

\* cited by examiner

Correlation of (x) with $T_3$

METHOD AND DEVICE FOR CONTROLLING TRANSMISSION POWER OF AN ACTIVE TRANSDUCER

BACKGROUND

The present disclosure is related to the field of active signal transducers. More specifically, the present disclosure relates to the control of the transmission power of an active transducer.

Many monitored signals may be characterized as quasi-periodic signals. These signals exhibit a generally repeating wave form, but at a constantly changing frequency. One such example of a quasi-periodic signal is a returned ultrasound signal exhibiting a Doppler effect such as from the motion of a fetus' beating heart. While ultrasound signals have a variety of applications in medical and other fields, including imaging, diagnostic, and therapeutic applications, one such application is the use of ultrasound signals to monitor fetal heart rate.

In the measurement of fetal heart rate, it is desirable to be able to determine the instantaneous period of the fetal heart rate at each heart beat. The determination of beat-to-beat fetal heart rate can have additional diagnostic value in determining the condition of the fetus compared to evaluating fetal condition based upon average fetal heart rate alone.

When monitoring fetal heart rate, it is often desirable to use a mobile device, such that the pregnant mother may remain ambulatory while the condition of the fetus is being monitored. Portable fetal heart rate monitors must rely upon battery power such that the pregnant mother is not restricted in her movements by a connection to a more permanent power source.

BRIEF DISCLOSURE

In the disclosed embodiment of a device for controlling the transmission power of an ultrasound signal produced by an ultrasound signal generator include a signal-to-noise ratio calculator. A fetal heart rate analysis selector selects between a first and second FHR analysis techniques, the selected technique being used to determine the fetal heart rate. A transmission power controller selects an optimal signal noise ratio range based upon the selected fetal heart rate analysis technique and compares the computed signal-to-noise ratio for the returned signal to the selected predefined optimal signal-to-noise ratio range, and produces a control signal which is sent to the ultrasound signal generated to modify the transmission power of the ultrasound signal generator.

An alternative embodiment of a signal analysis device for collecting and analyzing a quasi-periodic signal is disclosed herein. This embodiment of the signal analysis device includes a signal transducer that generates a stimulus signal at a transmission power and collects a return signal in response to the stimulus signal. A signal-to-noise calculator receives the returned signal and computes a signal-to-noise ratio of the returned signal. A signal analysis selector selects between a first signal analysis technique and a second signal analysis technique and produces a signal indicative of the selected technique. A transmission power controller receives the signal indicative of the selected signal analysis technique, selects a predefined optimal signal to noise ratio range for the selected technique, prepares the computer signal-to-noise ratio for the returned signal to the selected predefined optimal signal-to-noise ratio range, and produces a control signal which is sent to the signal transducer to modify the transmission power of the signal transducer such that the signal-to-noise ratio of the returned signal is modified to within the predefined optimal signal-to-noise ratio range for the selected signal analysis technique.

A method of operating an ultrasound signal generator is further disclosed herein. The embodiments of this method include generating a stimulus signal with the ultrasound signal generator at a transmission power. A returned signal is received in response to the stimulus signal. The signal-to-noise ratio of the returned signal is computed. Next, the signal-to-noise ratio is compared to a predetermined optimal signal-to-noise ratio range. Then, a control signal is sent to the ultrasound signal generator to control the transmission power of the stimulus signal generated by the ultrasound signal generator. Finally, a new stimulus signal is generated by the ultrasound signal generator at the transmission power specified by the control signal.

DETAILED DISCLOSURE

Many monitored signals are quasi-periodic signals. Often, it is desirable to accurately measure the instantaneous period of the signals. One such example of a quasi-periodic signal is the heart rate of an unborn fetus. This heart rate may be obtained by an ultrasound transducer that produces a constantly changing graph of the Doppler shift of the sound waves produced by the transducer as they are received after reflecting off of the fetus and passing through the mother's abdomen. While the present disclosure will focus on the example of monitoring fetal heart rate, it is to be understood that the present disclosure may be similarly applicable to a wide variety of other monitored quasi-periodic signals.

Signal transducers such as an ultrasound transducer can be referred to as an active transducer. In active transducers, a stimulus signal (i.e. the ultrasound signal) is generated by the transducer and applied to the subject of the monitoring. A signal is returned in response to the stimulus signal. This returned signal may either be an invoked potential, whereby the body produces a biopotential response to the stimulus signal, or may be a reflection of the stimulus signal, as is the case in ultrasound. In active signal transduction, the strength of the stimulus signal is closely related to the strength of the returned signal, and thus related to the quality of the analysis that may be performed using the returned signal. This is due to the fact that a stronger returned signal contains more data and is less susceptible to noise and other artifacts.

In remote monitoring situations, or monitoring situations in which the subject may not be remotely located, but subject mobility is of high importance, the monitoring may be performed using a portable device. These portable devices must rely upon a portable power source, such as a battery in order to supply the necessary power for both the signal monitor and data analysis operations. This presents a problem as often the noise in motion artifacts caused by an ambulatory patient require increased stimulus signal transmission power, thus creating a greater strain on the battery power supply, reducing battery life.

Figure 1:
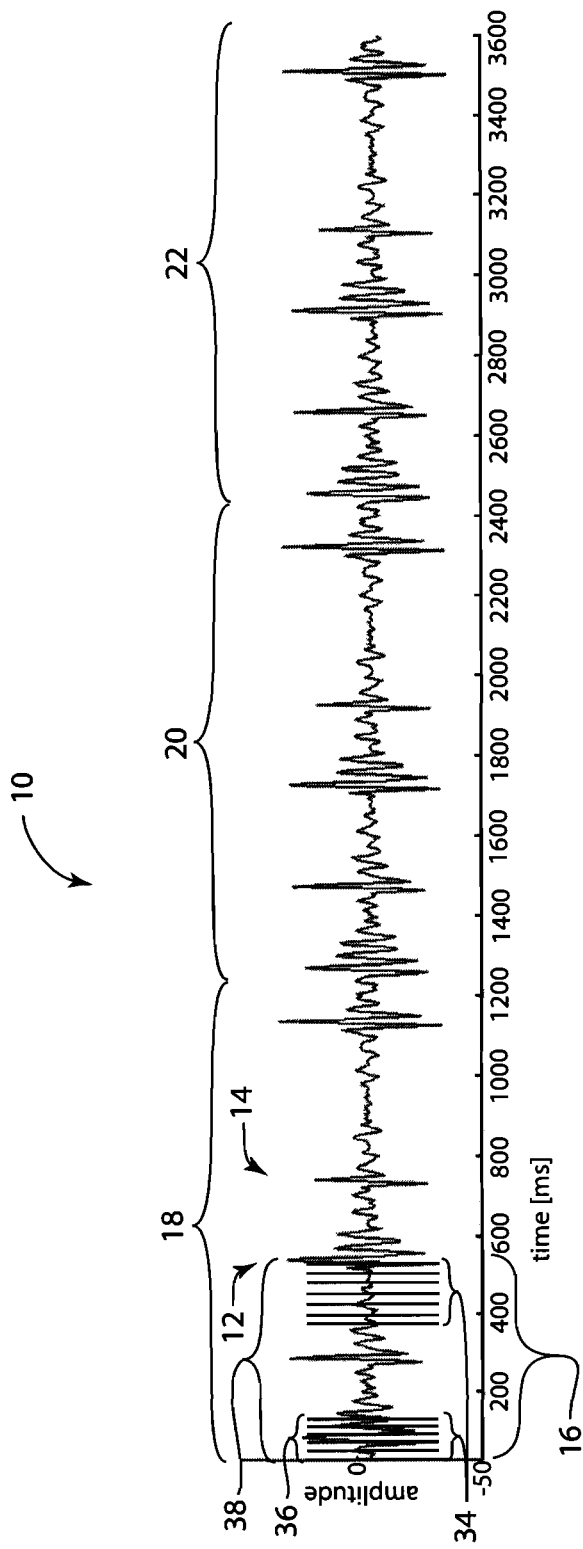
FIG. 1 is a diagram of an ultrasound signal.

FIG. 1 depicts an exemplary graph of an ultrasound signal 10 obtained when monitoring fetal heart rate. The ultrasound signal 10 includes a plurality of generally repeating waveforms. Each heart beat of the fetus registers in the ultrasound signal 10 as a complimentary pair of pulses corresponding to the two basic functional movements of the heart. The first wave form 12 corresponds to the contraction of the ventricles and the second wave form 14 corresponds to the closure of the semilunar valves. The ultrasound signal 10 of FIG. 1 is a quasi-periodic signal in that while the signal is generally repeating, the frequency of the signal is constantly shifting over a frequency range. The fetal heart frequently beats within a range of 30-300 beats per minute.

Figure 2A:
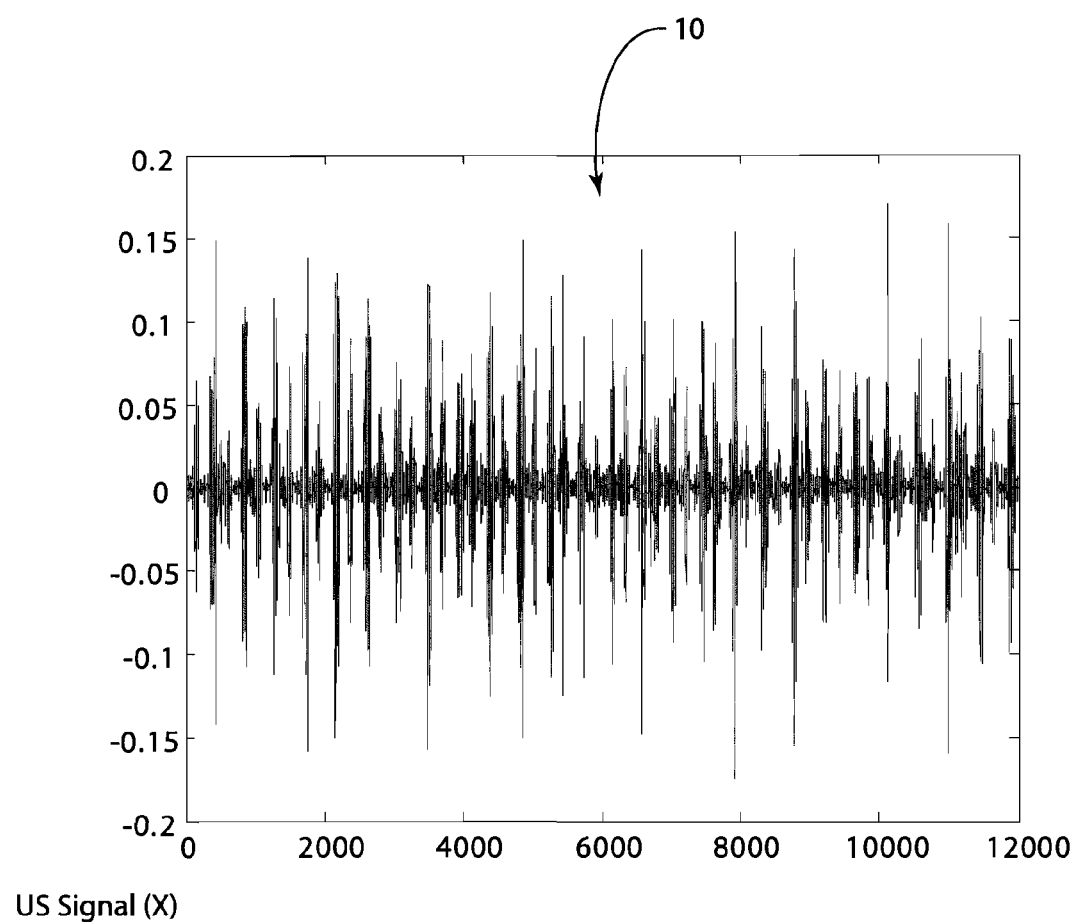
FIGS. 2A-D depict exemplary signals.
Figure 2B:
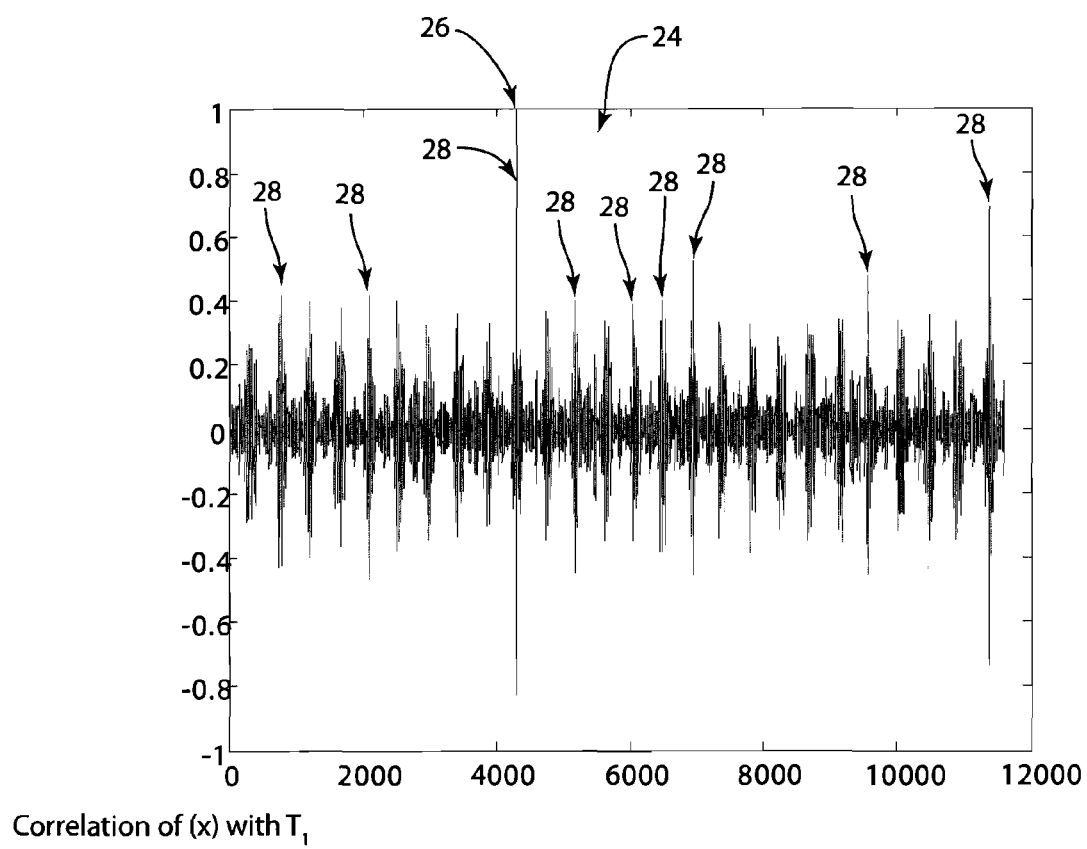
Figure 2C:
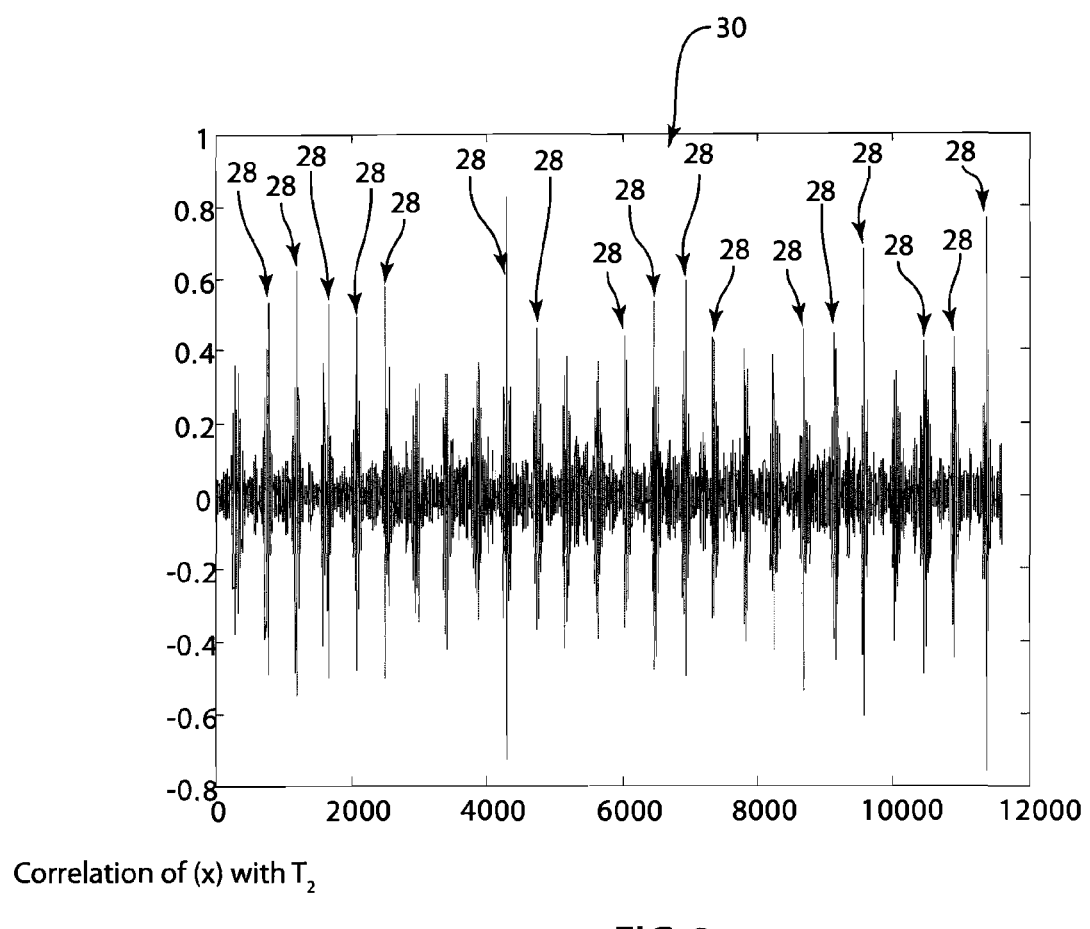
Figure 2D:
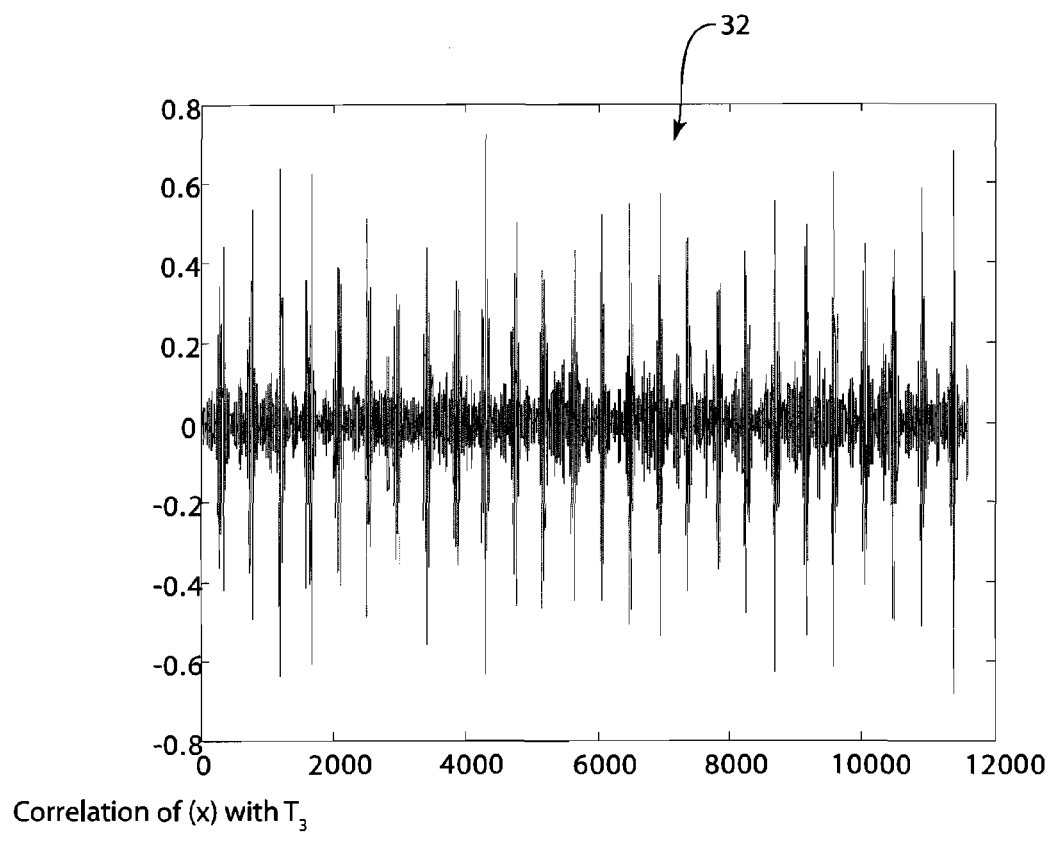
Figure 3:
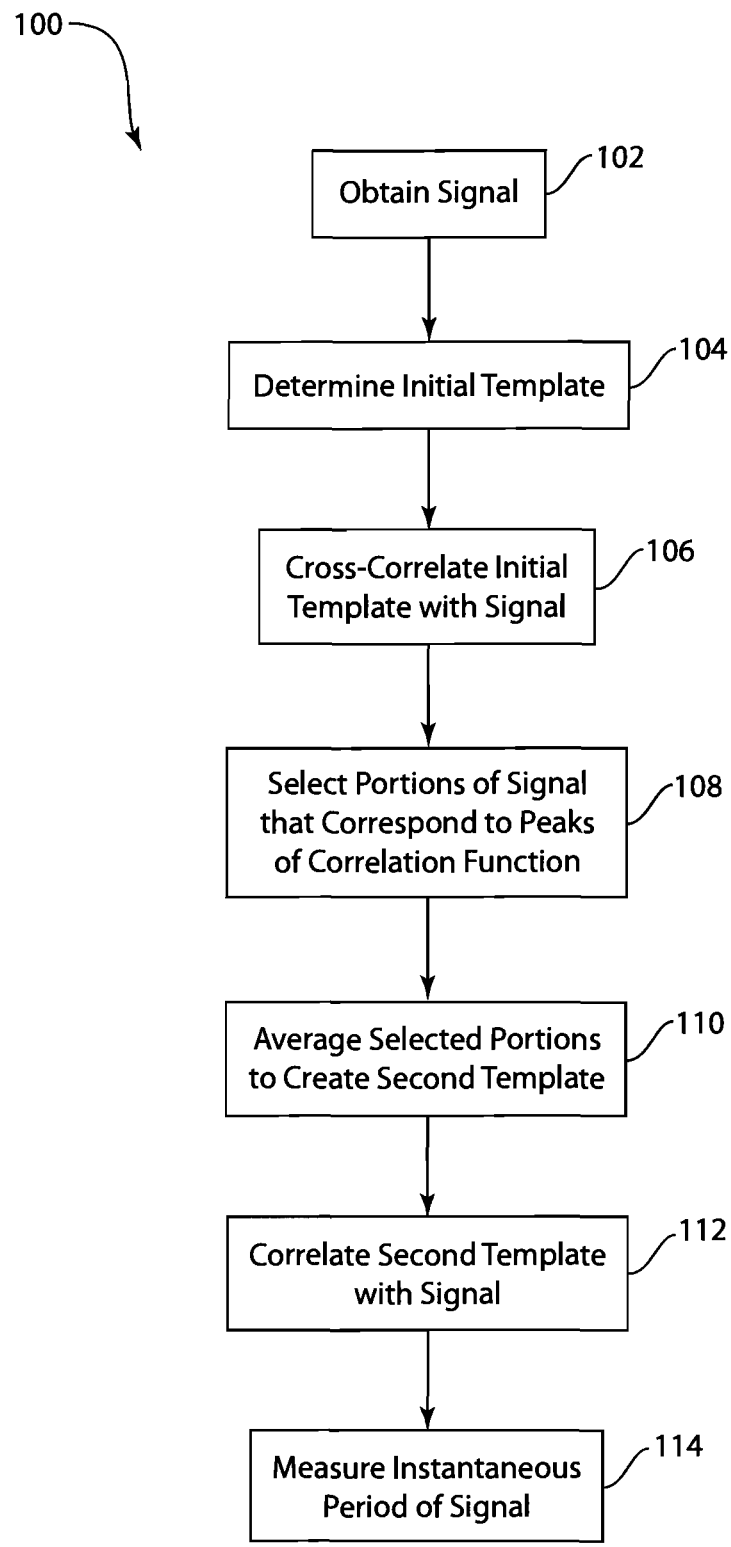
FIG. 3 is a flow chart depicting a general embodiment of the method for measuring the instantaneous period of a quasi-periodic signal.

FIG. 3 is a flow chart depicting the steps of an embodiment of a method for measuring the instantaneous period of a quasi-periodic signal, such as an ultrasound Doppler measurement of fetal heart rate. The steps depicted in FIG. 3 will be explained in greater detail herein with references to the graphs of FIGS. 1 and 2A-D.

First, a quasi-periodic signal, such as the Doppler shift of a returned ultrasound signal of fetal heart rate is obtained at step 102. This signal may be obtained through known ultrasound monitoring acquisition processes, or in the event of other applications, known methods or techniques used in acquiring the desired quasi-periodic signal. FIG. 2A is an exemplary graph depicting 27 beats of the returned ultrasound signal 10 including fetal heart signals mixed with unwanted noise. During the course of obtaining this signal, the returned ultrasound signal may be filtered with a band pass filter to remove frequency components and noise artifacts that are not associated with the fetal heart beat.

Next, an initial template is determined at step 104. Referring to FIG. 1, the initial template 16 may be selected of a determined temporal size and temporal shift. In one embodiment, this initial template is the signal associated with a single fetal heart beat.

Next, the previously determined initial template 16 is cross correlated with the ultrasound signal 10 at step 106. In some embodiments, the ultrasound signal 10 may be divided into segments, such as the exemplarily depicted first segment 18, second segment 20, and third segment 22. The initial segment 16 may then be cross correlated with one of the ultrasound signal segments (18, 20, 22) to create a correlation signal. Cross correlation is a common technique used to measure the similarity of two signals or signal segments, in this case, the initial segment 16 and the ultrasound signal 10. FIG. 2B depicts a graph of the first correlation signal 24 between the ultrasound signal 10 of FIG. 2A and an initial template selected from the ultrasound signal between sample numbers 4300 and 4700. Therefore, the first correlation signal 24 exhibits a maximized correlation peak 26 at the segment selected as the initial template.

Referring back to FIG. 3, at step 108, portions of the ultrasound signal 10 that correspond to the peaks of the first correlation signal 24 are selected. To identify the peaks of the first correlation signal 24, a peak amplitude threshold may be established. By way of example, a peak amplitude threshold of 0.4 may be selected and any correlation peaks that meet or exceed this threshold are selected. With reference to FIG. 2B, there are nine selected peaks 28 of the first correlation signal 24 and the portions of the ultrasound signal 10 that correspond to these peaks are selected.

At step 110, the selected portions of the ultrasound signal 10 are averaged to create a second template. Then, at step 112, the second template is cross correlated with the ultrasound signal 10 to create a second correlation function. FIG. 2C depicts a graph of the second correlation signal 30. By viewing this graph, it is noticeable that the amplitude peaks of the second correlation signal 30 are higher and more defined on average than those of the first correlation signal 24.

The instantaneous period of the fetal heart rate may be measured at step 114 for each heart beat using this more refined second correlation signal 30 and measuring the period between the correlation peaks.

In an alternative embodiment, the same 0.4 amplitude threshold or another determined threshold may be used to select correlation peaks from the second correlation signal 30 that meet or exceed the threshold. These selected peaks 28 of the second correlation signal 30 may be used to select the corresponding portions of the underlying ultrasound signal 10 such that these selected portions may be averaged to create a third template. The third template may in turn be cross correlated with the ultrasound signal 10 in order to produce a third correlation signal 32, which is depicted in FIG. 2D. Again, the amplitude of the correlation peaks of the third correlation signal 32 are on average higher and better defined than those of the second correlation signal 30. Thus, the third correlation signal 32 may alternatively be used to measure the beat-to-beat instantaneous period of the fetal heart.

Figure 4:
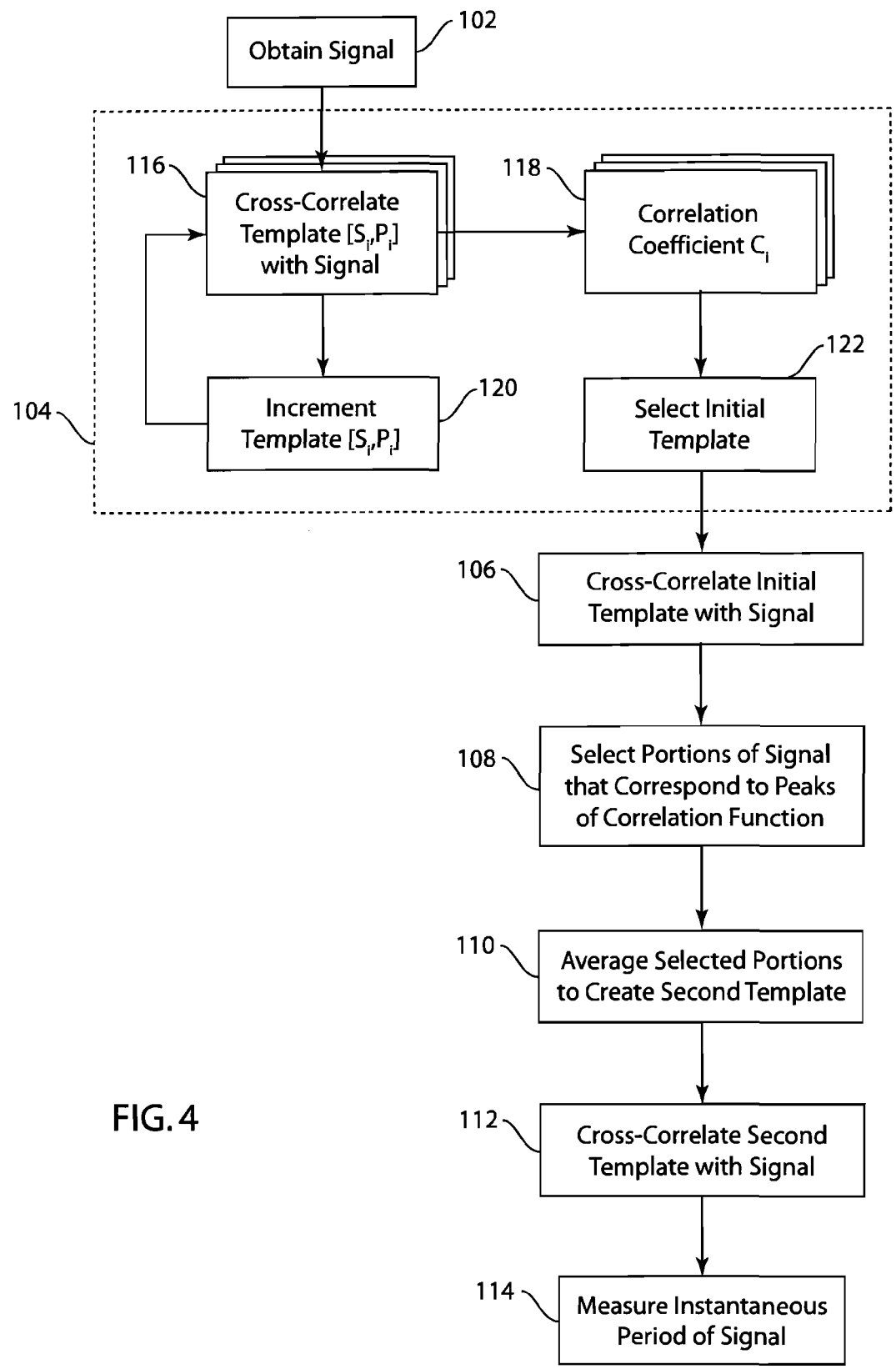
FIG. 4 is a more detailed flow chart of an embodiment of the method of FIG. 3.

FIG. 4 is a flow chart depicting a more detailed embodiment of the method depicted in the flow chart of FIG. 3. More specifically, the flow chart of FIG. 4 depicts a more detailed embodiment of the step of determining the initial template 104. As indicated in FIG. 1, the initial template is of a temporal size (S) and temporal shift (P). The initial template is determined by first selecting a template ($S_i$, $P_i$) from the ultrasound signal 10, or an ultrasound signal segment (i.e. first segment 18), and this template is cross correlated with the ultrasound signal 10 at step 116. This produces a correlation signal, and a corresponding correlation coefficient ($C_i$) is calculated at step 118. The correlation coefficient $C_i$ is a numeral value that represents the correlation between the template ($S_i$, $P_i$) and the signal 10. The correlation coefficient $C_i$ may be temporarily stored on a data storage medium that is internal or external to the system or device performing the disclosed method.

Next, at step 120, the template ($S_i$, $P_i$) is incremented in either the size of the template ($S_{i+1}$), the shift of the template ($P_{i+1}$), or both ($S_{i+1}$, $P_{i+1}$). These increments are denoted as reference number 34 in FIG. 1. Then, step 116 is repeated to cross correlate the new incremented template with the signal to obtain, at step 118, a new correlation coefficient ($C_{i+1}$). This correlation coefficient ($C_{i+1}$) is also temporarily stored on the data storage medium. These steps are repeated throughout a predetermined number of increments to the size and shift of the template in order to produce a plurality of correlation coefficients representing the correlation between each of the incremented templates and the signal. These correlation coefficients are all at least temporarily stored on the data storage medium. Then, at step 122, one of templates ($S_n$, $P_n$) is selected and stored to be the initial template. This selection of one template from all of the various templates created may be based upon the obtained corresponding correlation coefficients $C_n$ from step 118. The template ($S_n$, $P_n$) with the maximum correlation coefficient $C_n$ may be selected in step 122 as the initial template to be used in the rest of the steps of the method 100.

Figure 5:
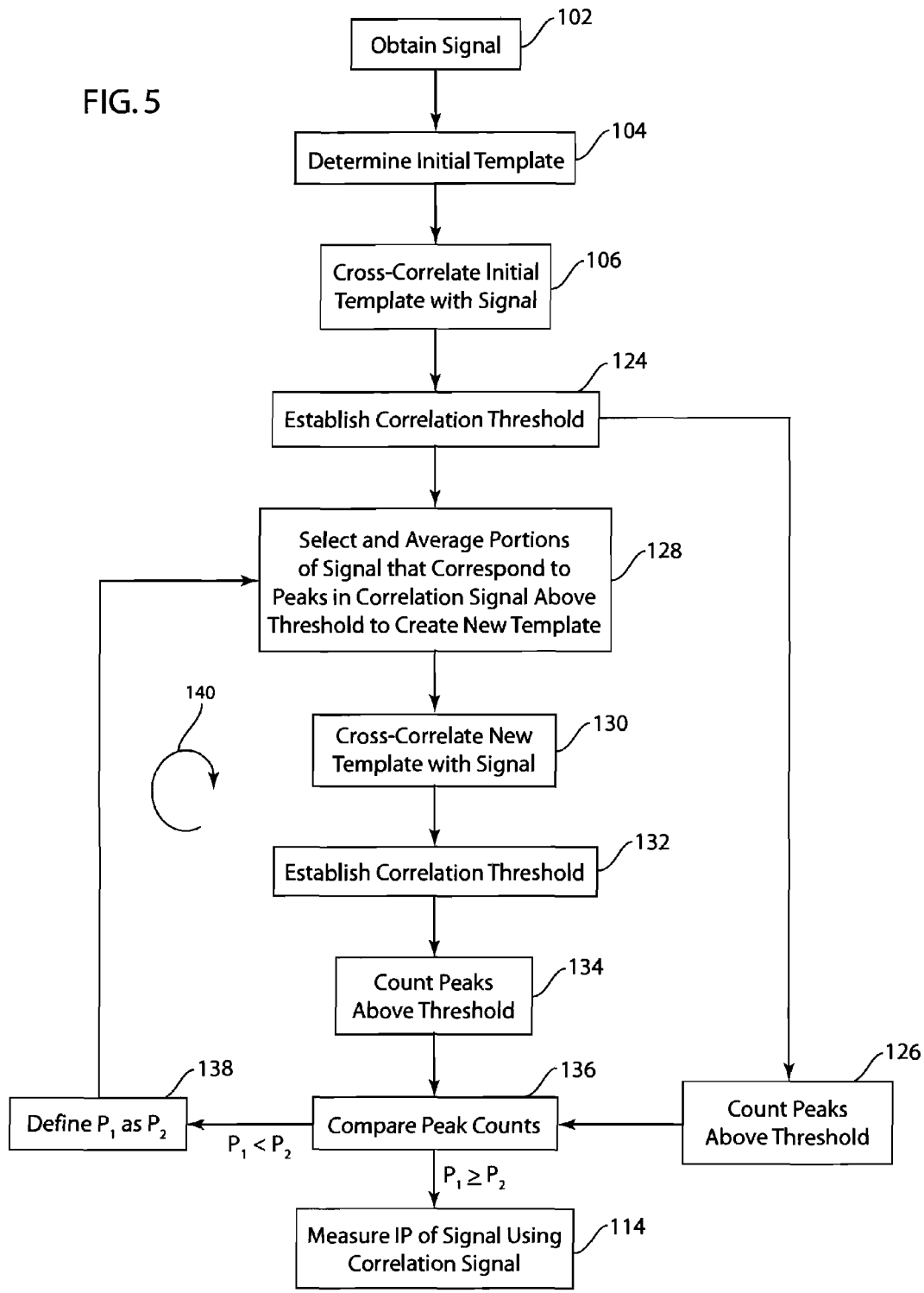
FIG. 5 is a flow chart that depicts the initial steps of an embodiment of the method for measuring the instantaneous period of a quasi-periodic signal.

FIG. 5 depicts a flow chart of a more detailed embodiment of the method 100 depicted in FIG. 3. The method depicted in the flow chart of FIG. 5 presents more detailed steps in the place of steps 108, 110, and 112 of the method 100 of FIG. 3.

In the method depicted in the flow chart of FIG. 5, after the initial template is cross correlated with the signal in step 106, a correlation threshold is established in step 124. At step 126, the correlation peaks above the threshold established in 124 are counted. The counted number of peaks is stored for later reference. In one embodiment, the counted number of peaks is stored as value $P_i$.

At step 128, the portions of the signal obtained in step 102 that correspond to the peaks in the correlation signal above the threshold established in step 124 are selected and averaged to create a new template. At step 130, the new template is cross correlated with the signal obtained in step 102.

Next, a correlation threshold is established at step 132 for the new correlation signal. The correlation threshold established in step 132 may be the same as the correlation threshold established in step 124 or may be adjusted according to another criteria or property of the signal such as would warrant the newly established correlation threshold in step 132 to be higher or lower than the one established in step 124. As an example, an elevated threshold in step 132 may be desirable to reflect the increased average amplitudes of the correlation peaks.

Then, at step 134, the peaks in the new correlation signal that exceed the correlation threshold established in step 132 are counted. The counted number of peaks in step 134 is stored for later reference. In one embodiment, the counted number of peaks is stored as the value $P_2$.

At step 136, the peak counts ($P_1$, $P_2$) from steps 126 and 134 are compared. If the peak count from step 126 is greater than or equal to the peak count ($P_2$) obtained in step 134, then the instantaneous period of the obtained signal is measured in step 114 using the new correlation signal. If, in step 136, the peak count ($P_1$) obtained in step 126 is less than the peak count ($P_2$) obtained in step 134, then peak count $P_1$ is redefined as the value of peak count $P_2$ at step 138 and the method is repeated with steps 128-136 through loop 140 with a newly created template using the peaks identified in step 134. The method of loop 140 may be repeated until at step 136, the peak count $P_1$ is greater than or equal to the peak count $P_2$, and the instantaneous period is measured in step 114.

Figure 6:
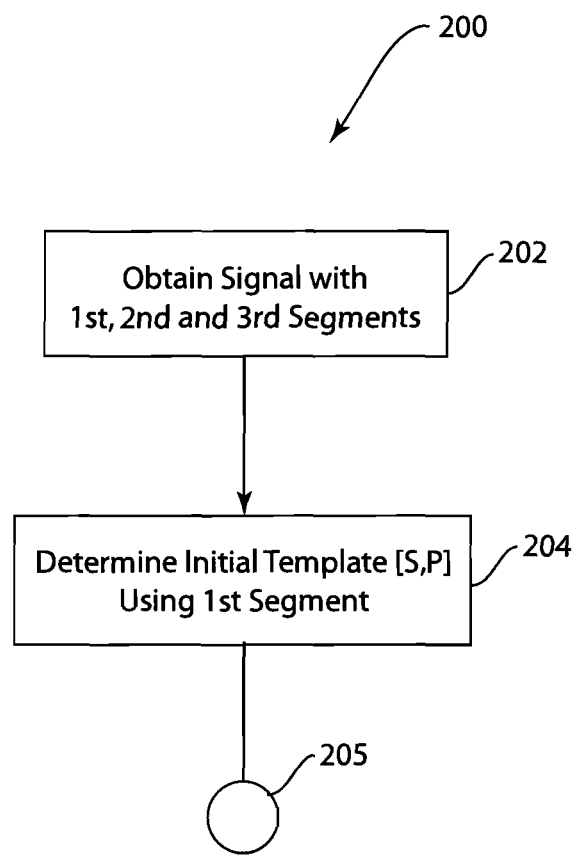
FIG. 6 depicts an alternative embodiment of a method for measuring the instantaneous period of a quasi-periodic signal.

FIG. 6 depicts the first two steps of an alternative embodiment of a method 200 of measuring the instantaneous period of a quasi-periodic signal. The method 200 includes the embodiments that will be disclosed herein with respect to the flow charts of FIGS. 7, 8, and 9. Referring back to FIG. 6, a signal with at least first, second, and third segments is obtained at step 202. The signal obtained in step 202 may be represented by the ultrasound signal 10 in FIG. 1 which has been divided into equally sized first segment 18, second segment 20, and third segment 22.

Back to the flow chart of FIG. 6, at step 204 an initial template with a size S and a shift P is determined using the first segment of the signal obtained in step 202. The method 200 of FIG. 6 terminates in node 205. Alternative embodiments of the method 200 are depicted in FIGS. 7, 8, 9a and 9b, continuing the method 200 from node 205.

The initial template is obtained in the manner previously described wherein the initial template may be a portion of the first signal segment of a predetermined time length or a previously stored model template. Alternatively, the initial template may be derived by cross correlating a plurality of incremented templates ($S_i$, $P_i$) to determine the incremented template with the greatest correlation coefficient with the first signal segment to use as the initial template.

Figure 7:
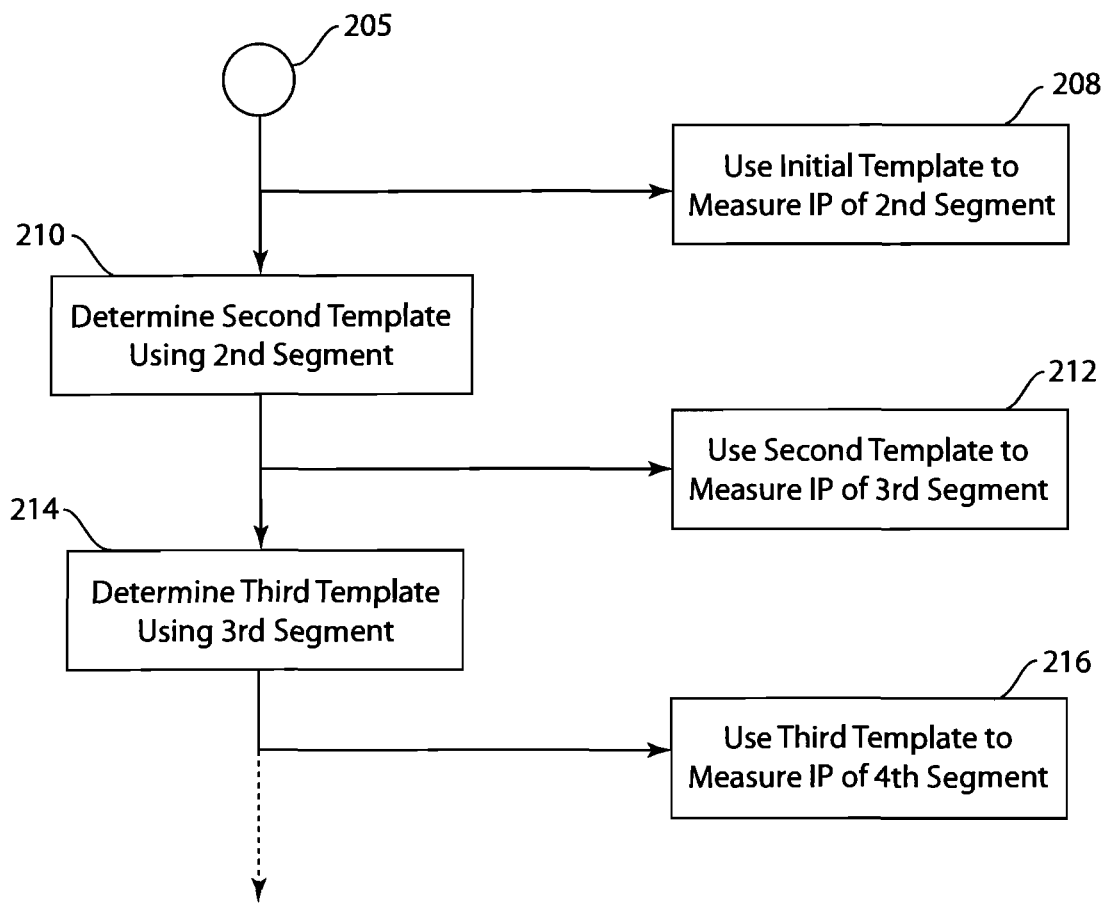
FIG. 7 is a flow chart depicting an embodiment of the steps continuing from the flow chart of FIG. 6.

Now referring to the embodiment of the method 200 depicted in the flow chart of FIG. 7, in step 208, the initial template from step 204 is used to measure the instantaneous period of the second segment. This is performed by cross correlating the initial template with the second signal segment to produce a second correlation signal from which the instantaneous period of the second signal segment may be obtained.

In step 210, a second initial template is determined using the second segment. The second initial template may be determined in the same manner as the initial template was; however, in this step, the second signal segment is used. Therefore, the second initial template may be derived by cross correlating a plurality of incremented templates ($S_i$, $P_i$) to determine the incremented template with the greatest correlation coefficient with the second signal segment to use as the second initial template.

Next, at step 212, the second initial template is used to measure the instantaneous period of the third signal segment. This is done by cross correlating the second initial template with the third signal segment to obtain a third correlation signal from which the instantaneous period is measured.

In some embodiments, the obtained signal may comprise more than a first, second, and third segment. In these embodiments, the method may continue in the following manner as will be described for a fourth segment for as many segments are in the obtained signal.

In step 214, a third initial template is determined using the third signal segment. The third template may be determined in the same manner as the initial template and second initial templates were determined. The third initial template is then used in step 216 to measure the instantaneous period of the fourth signal segment. This is done by cross correlating the third initial template with the fourth signal segment in order to obtain a fourth correlation signal. The instantaneous period of the fourth signal segment may be measured from the fourth correlation function.

Thus, the embodiment of the method disclosed in the flow chart of FIG. 7 may be used as a method for processing a continuously running quasi-periodic signal that may be divided into any number of segments and processed with an updated initial template by updating the initial template with each newly processed signal segment and applying the updated initial template to the newly collected segment of the obtained quasi-periodic signal.

Figure 8:
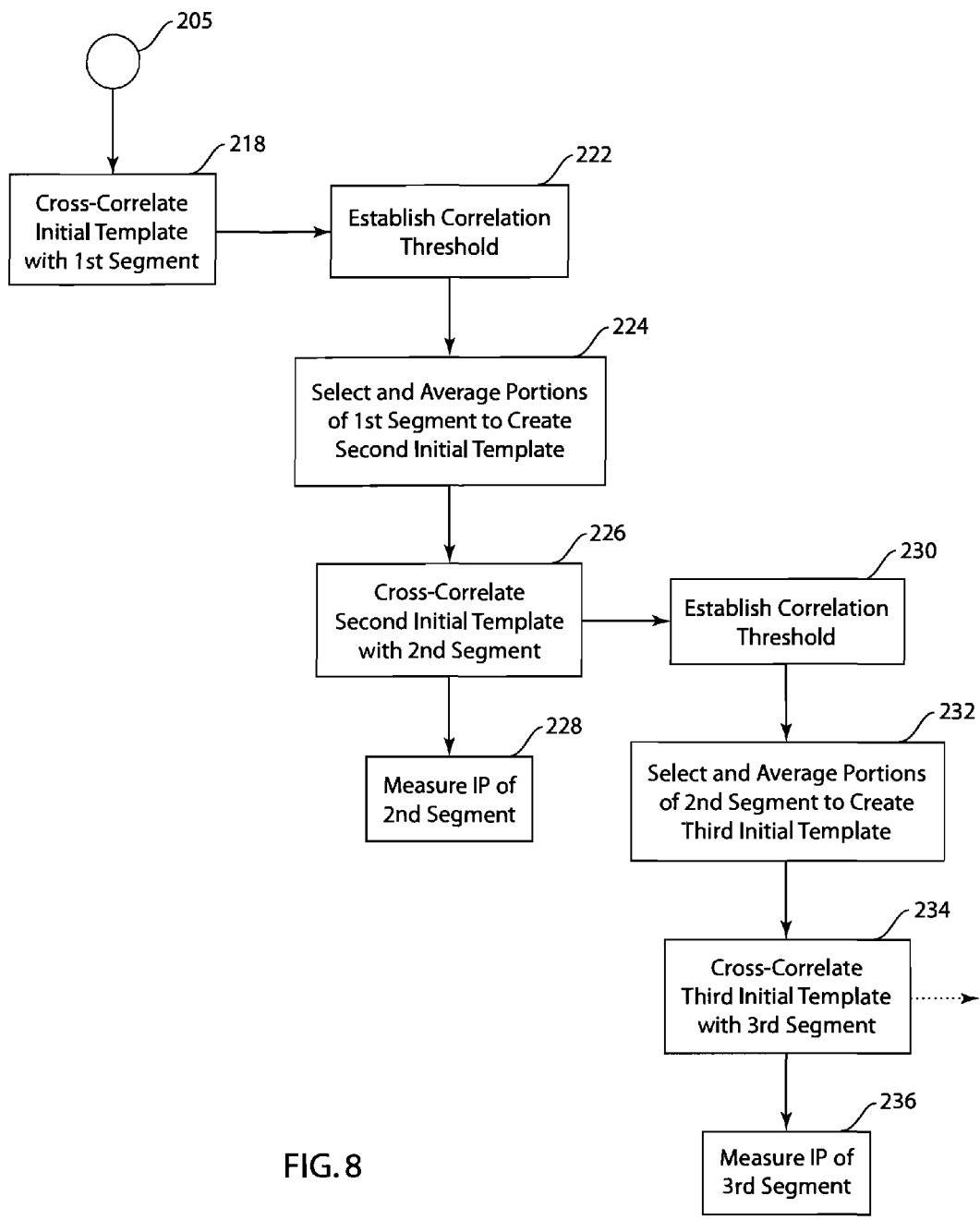
FIG. 8 is a flow chart depicting an embodiment of the steps continuing form the flow chart of FIG. 6.

FIG. 8 depicts a flow chart of an alternative embodiment of the method 200 starting in FIG. 6. In the embodiment depicted in the flow chart of FIG. 8, the initial template from step 204 is cross correlated with the first signal segment in step 218. This cross correlation produces a first correlation signal exhibiting a plurality of correlation peaks.

In step 222, a correlation threshold is established for use with the first correlation signal from the cross correlation of step 218. In step 224, the established correlation threshold is used to select portions of the first signal segment that correspond to the peaks in the first correlation signal that exceed the established threshold. The selected portions of the first signal segment are averaged to create a second initial template.

The second initial template is cross correlated in step 226 with the second signal segment to produce a second correlation signal exhibiting a plurality of correlation peaks. At step 228, the instantaneous period of the second signal segment is measured using the second correlation signal.

In step 230, a correlation threshold for the second correlation signal is established. In step 232, the correlation threshold is used with the second correlation signal to select the portions of the second signal segment that correspond to the peaks of the second correlation signal that exceed the correlation threshold. The selected portions of the second signal segment are averaged in step 232 to create a third initial template.

The third initial template is cross correlated with the third signal segment in step 234 to produce a third correlation signal. The third correlation signal includes a plurality of correlation peaks. The third correlation signal is used in step 236 to measure the instantaneous period of the third segment. The instantaneous period is measured by measuring the period between correlation peaks.

The above disclosed steps of the embodiment of the method 200 of the flow chart in FIG. 8 may be continuously repeated in the above-described fashion in order to process an obtained quasi-periodic signal with more than three segments. In the alternative, this embodiment of the method 200 may be used to process a continuously obtained quasi-periodic signal wherein the currently obtained segment of the signal is processed with an initial template created from the data of the previously obtained segment of the same signal. Thus, over the course of processing the continuously obtained signal, the template used to determine the instantaneous period of the signal is continuously updated to maintain accuracy in the instantaneous period determination.

Figure 9A:
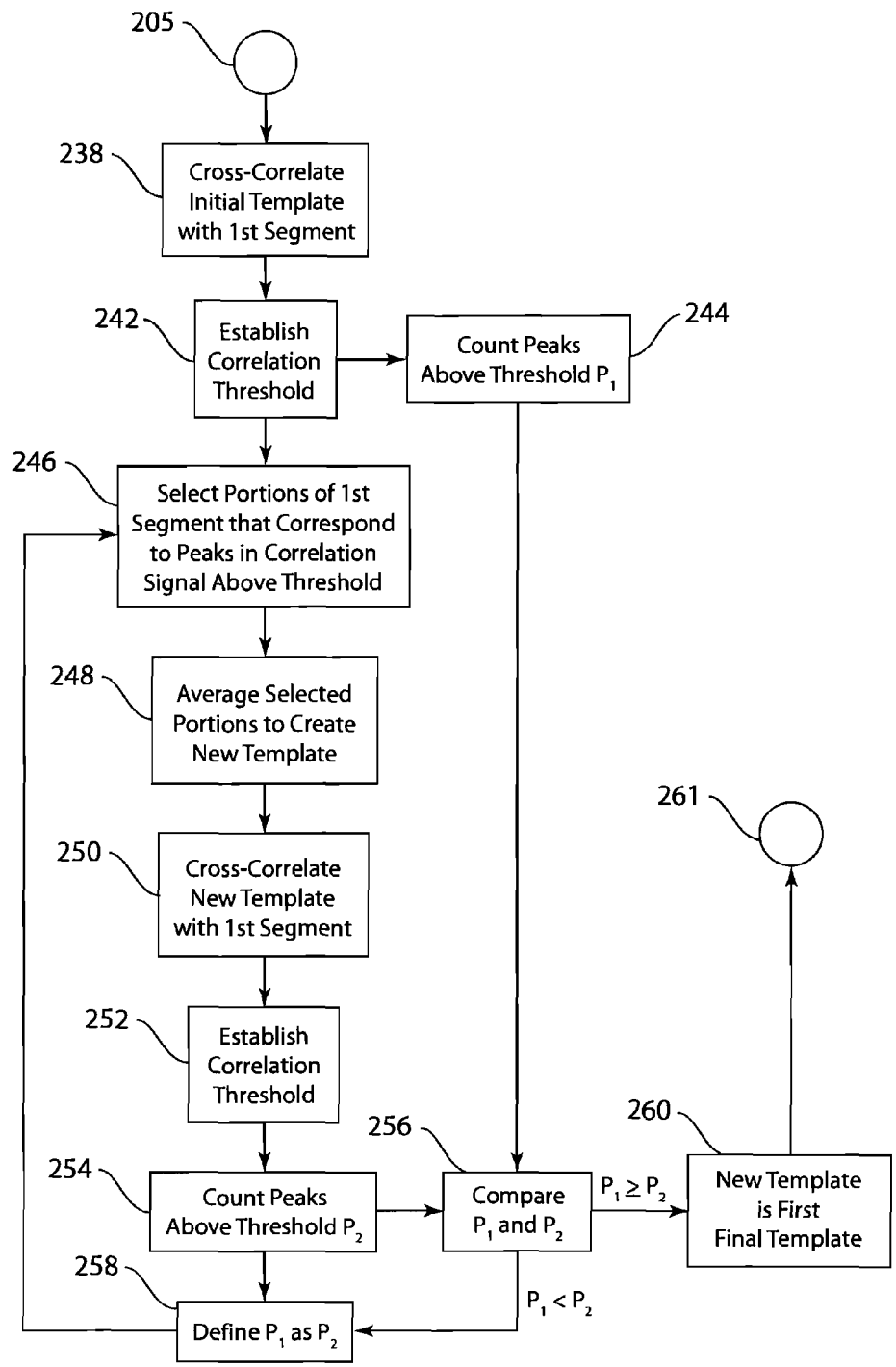
FIG. 9 is a flow chart depicting an alternative embodiment of the steps continuing from the flow chart of FIG. 6.
Figure 9B:
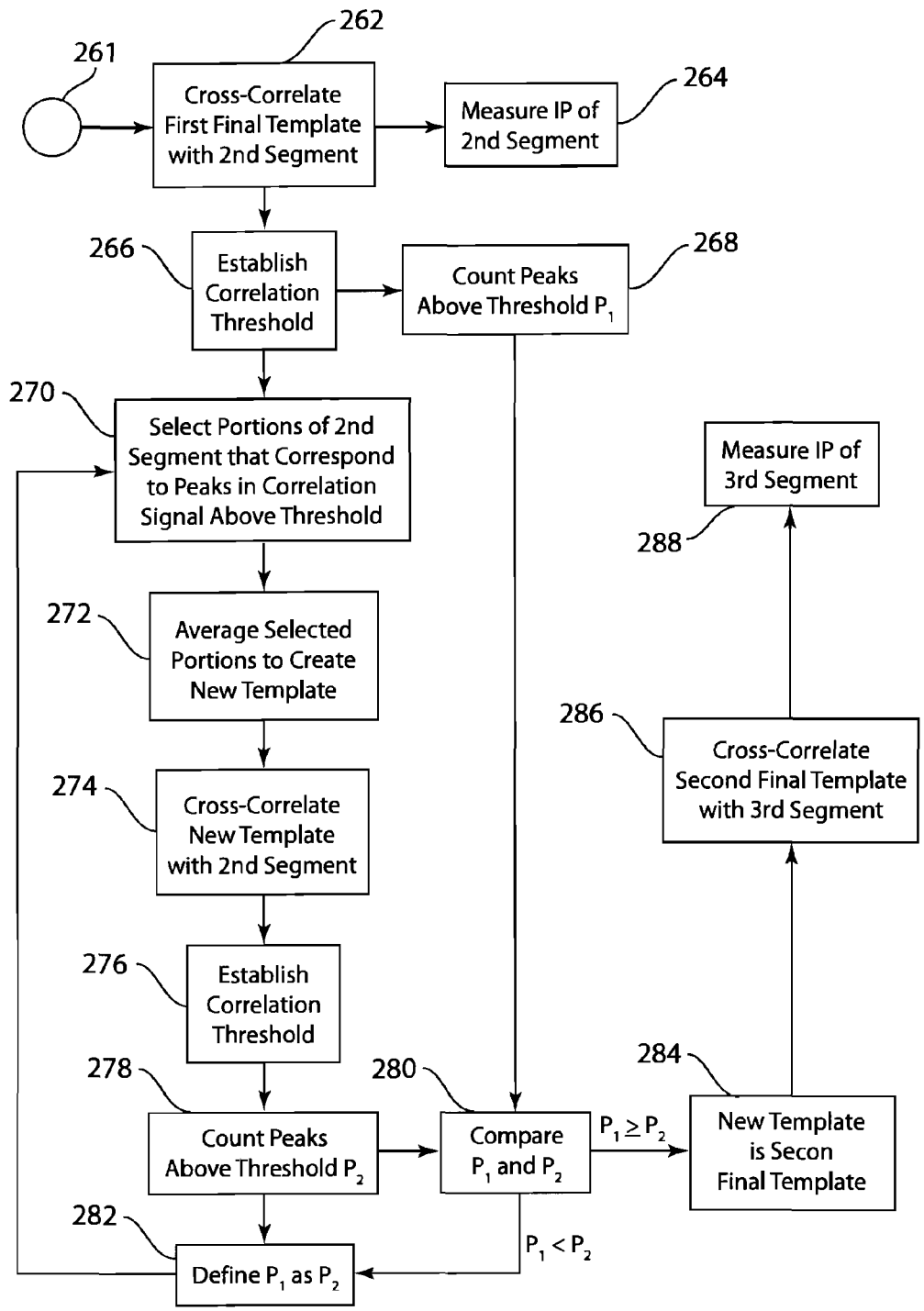

FIGS. 9a and 9b depict a flow chart of a still further embodiment of the method 200 continued from FIG. 6. In this embodiment, the template used to produce the correlation signal from which the instantaneous period is measured is maximized for each segment before it is applied to the next signal segment to measure the instantaneous period of the signal during that segment.

At step 238, the initial template is cross correlated with the first signal segment of the obtained signal, resulting in the first correlation signal. A correlation threshold is established in step 242 and the number of correlation peaks in the first correlation signal that exceed the established threshold are counted and this count is stored, for example, as value $P_1$ in step 244.

Next, portions of the first signal segment that correspond to the correlation peaks in the first correlation signal above the established threshold are selected in step 246. In step 248, these selected portions of the first signal segment are averaged to create a new template. In step 250, the new template is cross correlated with the first signal segment to obtain a new correlation signal. A correlation threshold for the new correlation signal is established in step 252 and in step 254 the correlation peaks that exceed the correlation threshold established in step 252 are counted. This count of the correlation peaks is stored, for example, as value $P_2$. It is to be understood that in some embodiments, the correlation threshold established in step 252 may be the same correlation threshold as is established in step 242; however, in other embodiments, a new correlation threshold may be established for each new correlation signal in order to more accurately control the counted number of correlation peaks.

In step 256, the count of the correlation peaks from step 244 represented as value $P_1$ and the count of the correlation peaks from step 254 represented by value $P_2$ are compared. If the count $P_1$ is less than the count $P_2$ then the value $P_1$ is redefined in step 258 as the current value of $P_2$ and steps 246 through 254 are repeated to obtain a new value for $P_2$ for comparison at step 256. If the value $P_1$ is greater than or equal to the value of $P_2$, then at step 260 the new template created in step 248 is stored as the first final template.

FIG. 9b continues from node 261 wherein the method of FIG. 9a left off. The first final template is then cross correlated in step 262 with the second signal segment to produce a second correlation signal. The second correlation signal is used in step 264 in order to measure the instantaneous period of the second signal segment. The instantaneous period may be measured by measuring the period between each correlation peak of the second correlation signal. Additionally, at step 266, a correlation threshold is established for the second correlation signal and at step 268 the correlation peaks above the correlation threshold are counted and may be stored as value $P_1$. The correlation threshold in step 266 is also used in step 270 wherein the portions of the second signal segment are selected that correspond to the correlation peaks in the second correlation signal that exceed the correlation threshold. In step 272, the selected portions of the second signal segment are averaged to create a new template.

In step 274, the new template is cross correlated with the second signal segment to produce a new correlation signal. Next, a correlation signal threshold is established in step 276 for the new correlation signal. In step 278, the correlation peaks in the new correlation signal that exceed the threshold established in step 268 are counted and may be stored as value $P_2$.

In step 280, the values of $P_1$ and $P_2$ are compared to each other. If the value $P_1$ is less than the value $P_2$, then in step 282 value $P_1$ is redefined as the current value of $P_2$ and steps 270 through 278 are repeated to establish a new value of $P_2$. Then again in step 280, the values of $P_1$ and $P_2$ are compared. The comparison in step 280 thus provides a loop whereby successive new templates and correlation signals are created for the second signal segment, with each new template being created using a greater number of segments of the second signal segment as the templates used become more accurate. The loop ends at step 280 when the correlation signal from the new template yields less than or equal the number of correlation peaks above the established threshold than the previous template did over the same second signal segment.

At this point, the current new template is defined to be the second final template at step 284. This is due to the fact that no more correlation peaks were identified with the new template, than with the previous template, which was evidenced by the value $P_1$ being equal to or greater than the value $P_2$. The second final template is then cross correlated with the third signal segment in step 286 to produce a third correlation signal. The third correlation signal is used in step 288 to measure the instantaneous period over the course of the third signal segment.

As with previously disclosed embodiments, the currently described embodiment may be likewise applied to signals obtained with more than three segments, or a continuously obtained signal that is incrementally divided into segments as it is obtained. In viewing the operation of the embodiment of the method 200 of FIG. 9, derivation of the first final template may require multiple cycles of steps 246 through 254; however, for the subsequent signal segments, relatively few cycles may be needed as only minor adjustments to the template may be required for each new signal segment.

In an alternative embodiment of the method 200 described with respect to FIGS. 9a and 9b, after or concurrent to step 252 of cross correlating the first final template with the second segment, the additional step of determining a new initial template (S,P) from the second segment (not depicted) is performed.

The new initial template may be determined as previously described above, starting with a template of a temporal size (S) and a temporal shift (P). The new initial template is determined by first selecting a template $(S_i, P_i)$ from the second segment, and this template is cross correlated with the second segment. This produces a correlation signal and a corresponding correlation coefficient $(C_1)$. Next, the template $(S_i, P_i)$ is incremented in either the size of the template $(S_{i+1})$, the shift of the template $(P_{i+1})$ or both $(S_{i+1}, P_{i+1})$. Then, the cross correlation is repeated using the new incremented template and the second segment to obtain a new correlation coefficient $(C_{i+1})$. These steps are repeated throughout a predetermined number of increments to the size and shift of the template in order to produce a plurality of correlation coefficients representing the correlation between each of the incremented templates and the signal.

One of the templates $(S_n, P_n)$ is selected and stored to be the initial template. The selection of one template from all of the various templates created may be based upon the obtained corresponding correlation coefficients $C_n$. The template $(S_n, P_n)$ with the maximum correlation coefficient $C_n$ may be selected as the initial template that is to be cross correlated with the second segment. The correlation signal from the cross correlation between the new initial template and the second segment is then used in steps 266 and 268 to identify the correlation peaks that are above the established correlation threshold.

In this disclosed alternative embodiment, a new final template is created using not only the iterave process of refining the template, but using a new initial template for each of the segments of the quasi-periodic signal to be analyzed.

In still further alternatives to the method embodiments disclosed with respect to FIGS. 6-9, after the initial template (S, P) has been determined using the first segment in step 204, an output may be produced that identifies the instantaneous period of the first segment. As a practical matter, this determination may often be delayed, in that in typical embodiments, the template produced from the previous segment is used to analyze the next segment of the quasi-periodic signal. Therefore, in some embodiments, no measurement of instantaneous period is obtained for the first signal segment as the initial template is used to measure the instantaneous period of the second segment. However, in other embodiments, other methods for determining instantaneous period may be used to provide an analysis or an estimation of the instantaneous period of the first signal segment. These analyses may include short term analysis (STA) or other forms of analysis whereby the first period of the first segment, or other peak detection techniques are used to determine, or estimate, the instantaneous period of the quasi-periodic signal over the first signal segment.

Figure 10:
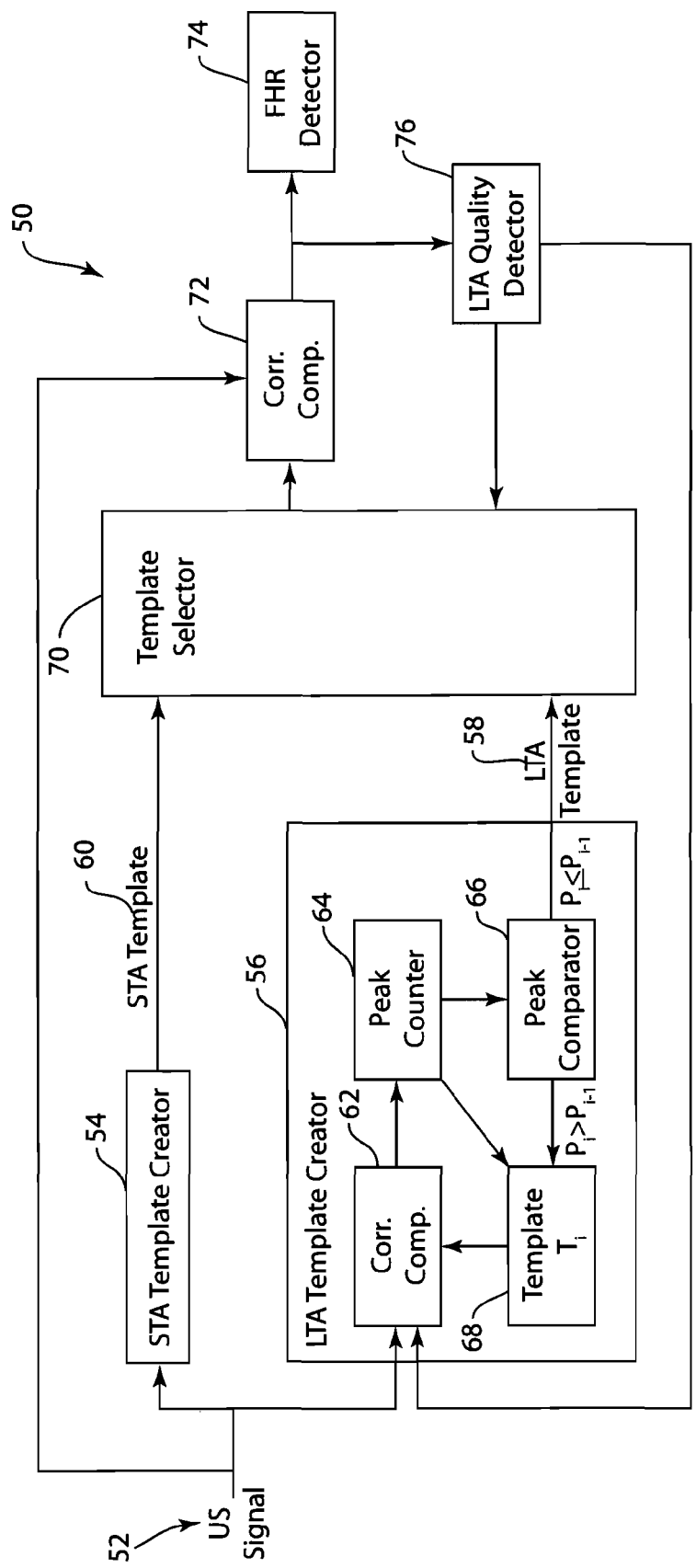
FIG. 10 is a system diagram of an embodiment of a system for measuring the instantaneous period of a quasi-periodic signal.

FIG. 10 depicts an embodiment of a system 50 for measuring the instantaneous period of quasi-periodic signal. The system 50, which more specifically, is one embodiment for obtaining the instantaneous fetal heart rate from a returned ultrasound signal. The quasi-periodic returned ultrasound signal 52 is obtained from an ultrasound transducer through commonly known ultrasound techniques. The returned ultrasound signal is provided to a short term analysis (STA) template creator 54. The STA template creator creates a short term analysis template 60 for analysis of the returned ultrasound signal 52. The short term analysis template 60 may be a predefined model STA template or may be a selected portion of the returned ultrasound signal 52. If the STA template 60 is a selected portion of the returned ultrasound signal 52, then the selected portion is of a generally short duration, for example, on the order of 1-2 seconds of data.

The returned ultrasound signal 52 is also provided to a long term analysis (LTA) template creator 56. The LTA template creator operates according to one of the methods as disclosed herein to produce a long term analysis template 58. The LTA template creator 56 includes a correlation computer 62 that correlates a template $T_i$ with the ultrasound signal 52, or a segment thereof. A peak counter 64 either defines or uses a predetermined correlation threshold in order to identify and count the correlation peaks of the correlation signal received from the correlation computer 62. The peak counter 64 produces a count $(P_i)$ of the peaks meeting or exceeding the correlation threshold.

A peak comparator 66 compares the number of peaks $(P_i)$ counted by the peak counter 64 for the current correlation signal compared to the number of peaks $(P_{i-1})$ counted by the peak counter 64 for the previous correlation signal. If the number of peaks counted for the current correlation signal $(P_i)$ exceeds the number of peaks counted for the previous correlation signal $(P_{i-1})$, then a template creator 68 averages the portions of the ultrasound signal that correspond to the peaks in the correlation signal detected by the peak counter 64 to create a new template $T_i$. The new template from template creator 68 is then applied to the same segment of the ultrasound signal by the correlation computer 62.

This process is repeated until the peak counter 64 identifies a number of peaks less than or equal to the number of peaks identified in the previous correlation signal. When the peak comparator 66 identifies that this condition is met, the current template $T_i$ is the LTA template 58 which is provided to the template selector 70. The template selector 70 receives both the LTA template 58 and the STA template 60. The template selector 70 selects one of the STA template 60 or the LTA template 58 to provide to the correlation computer 72. The correlation computer 72 also receives the ultrasound signal 52 and cross correlates the template selected by the template selector 70 with the ultrasound signal 52 to produce a correlation signal. This correlation signal is used by an FHR detector 74 to determine the instantaneous fetal heart rate in the ultrasound signal 52.

The correlation signal from the correlation computer 72 is also provided to an LTA quality detector 76. The LTA quality detector 76 determines the quality of the instantaneous fetal heart rate detection capability of the correlation signal produced by the correlation of the current LTA template 58 with the ultrasound signal 52. The LTA quality detector 76 may operate in a number of ways such as may be used to evaluate the quality of a signal obtained through signal processing. One exemplary embodiment of a methodology for the LTA quality detector 76 is that the LTA quality detector 76 constantly performs a correlation between the STA template 60 and the ultrasound signal 52.

Alternatively, the LTA quality detector 76 may receive the results of the cross correlation between the STA template 60 and the ultrasound signal 52 from another source. The LTA quality detector 76 may then compare the correlation signal from the STA template 60 versus the correlation signal from the LTA template 58. If the STA template 60 produces a correlation signal with the greater amplitude of correlation peaks, then the LTA quality detector 76 may indicate that the LTA template quality is low. If, on the other hand, the cross correlation of the LTA template 58 and the ultrasound signal 52 produces a correlation signal with the maximum amplitude correlation peaks compared to the correlation signal from the STA template 60, then the LTA quality detector 76 may indicate that the LTA template quality is high.

In a still further embodiment, the LTA quality detector 76 may calculate the signal to noise ratio (SNR) for the correlation signal produced using the LTA template 58. The calculated SNR may be compared to a predetermined scale for acceptable LTA correlation signals to determine LTA quality. Alternatively, the LTA quality detector 76 may also calculate the SNR for the correlation signal from the STA template 60 and compare the calculated LTA and STA SNR values to determine LTA template quality.

The LTA quality detector 76 provides the high/low LTA quality determination to both the template selector 70 as well as the correlation computer 62 of the LTA template creator 56. The template selector 70 operates such that when the template selector 70 receives an indication of a high quality LTA template, the template selector 70 selects the LTA template 58 to provide to the correlation computer 72. If the template selector 70 receives an indication of a low quality LTA template, then the template selector 70 selects the STA template 60 to provide to the correlation computer 72.

The LTA template creator 56 operates in conjunction with the template selector 70 such that when the LTA template creator 56 receives an indication that the LTA template quality is low, then the LTA template creator 56, and more specifically the correlation computer 62 of the LTA template creator 56, begins the process of creating a new LTA template 58 to replace the current LTA template which has been deemed to be producing a low quality result. Similarly, once the LTA quality detector 76 has indicated that the current LTA template 58 is resulting in a high quality correlation signal, then the LTA template creator 56 stops its calculation of a new LTA template.

The system as disclosed in FIG. 10 provides the signal processing advantage of optimizing the instantaneous fetal heart rate detection between short term analysis and long term analysis methods. The short term analysis method has the advantage of being constantly available to analyze the ultrasound signal as it uses a predefined STA template. As disclosed herein, the LTA method of instantaneous fetal heart rate detection produces an improved quality of result; however, experiences a lag time as the LTA template must be created from collected ultrasound signal data. Also, the LTA analysis method has the further challenge of resulting in a correlation signal of a varying quality. This requires the need to periodically update the LTA template to maintain a high quality correlation signal.

Thus, the system 50 provides a solution to these problems by providing the STA template for a base level of instantaneous fetal heart rate detection while the LTA template is unavailable for instantaneous fetal heart rate detection. However, once the LTA template becomes available for a high quality instantaneous FHR detection, the system 50 switches over to the LTA method of analysis to produce a higher quality of instantaneous FHR detection.

As referred to earlier, the monitoring of a quasi-periodic signal may be performed in a situation in which the quasi-periodic signal is monitored by a system that is powered by a portable power source, such as a battery. In these situations, the active transducer used to monitor the quasi-periodic signal is a user of a large amount of energy from the battery. In many applications, the more noise that is present in the desired signal, the stronger the required stimulus signal in order to obtain the quasi-periodic signal for a high quality analysis. In order to maximize the life of the portable power source, or battery, it is desirable to operate the signal transducer in a fashion that uses the minimal excitation signal transmission power needed for the desired quality of data analysis.

As has been heretofore disclosed in the present application, long term signal analysis may be used in order to produce improved quasi-periodic signal analysis. One application of the disclosed long term analysis system and methods is to additionally control the transmission power of a signal transducer based upon the type of signal analysis (long term analysis or short term analysis) currently being performed. During long term analysis of the quasi-periodic signal, the improved signal analysis capability afforded by the LTA may be used to reduce the transmission power of the signal transducer while maintaining a desired level of signal analysis quality, such as the signal analysis quality of the STA technique. Thus, the transmission power can be comparatively reduced from the greater amount required for the STA technique.

Figure 11:
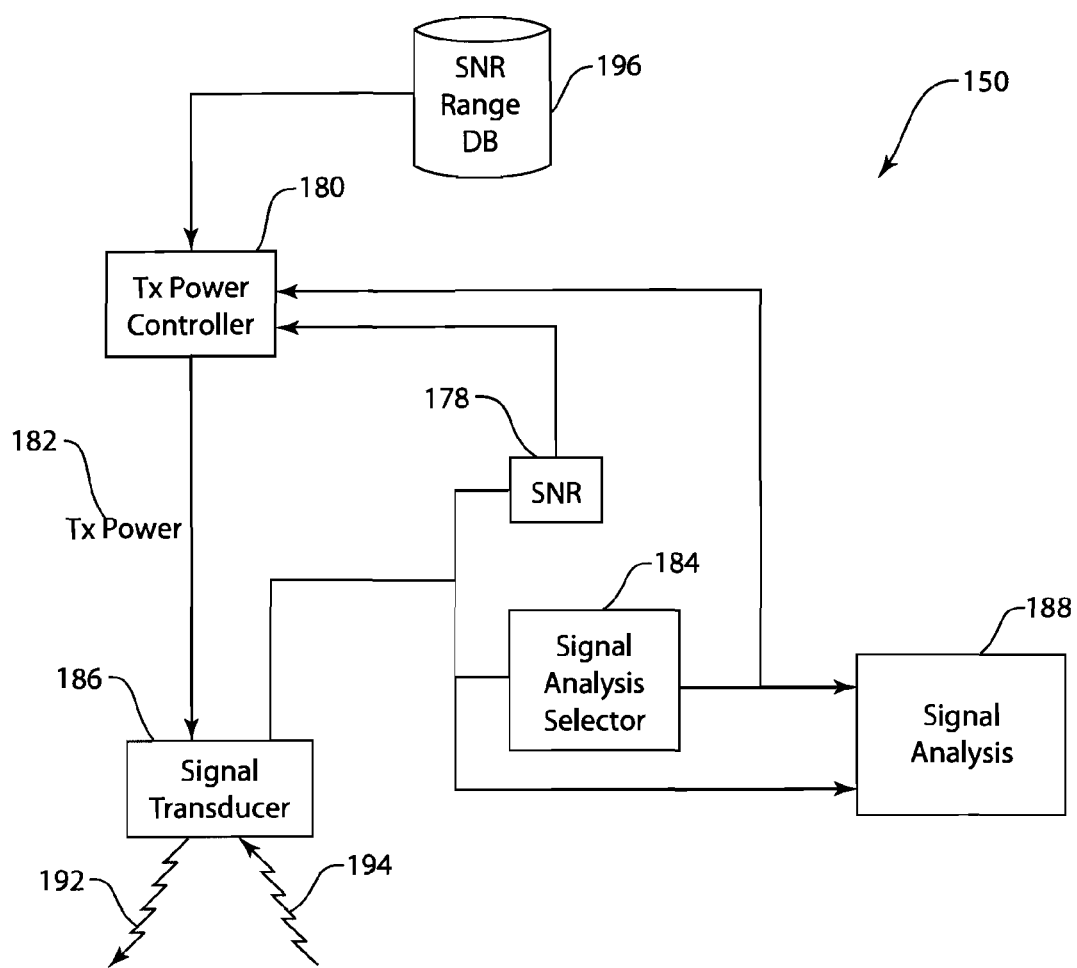
FIG. 11 depicts a signal analysis device with transmission power control for collecting and analyzing a quasi-periodic signal.

FIG. 11 depicts a transmission power control device 150. The transmission power control device 150 includes a signal transducer 186 that produces a stimulus signal 192 and receives a returned signal 194. The signal transducer 186 may be that of an ultrasound transducer, or may be another form of active transducer such as an electrode. The stimulus signal 192 may be a sound wave as in the case of the ultrasound transducer, or may be an electrical impulse such as would be provided by an electrode. Alternative embodiments of the signal transducer 186 may produce a stimulus signal 192 of a mechanical or other type of origin. In response to the stimulus signal 192, a returned signal 194 is received by the signal transducer 186. The returned signal 194 may be a biopotential, displacement, or change in pressure by the subject being monitored in response to the stimulus signal 192. Alternatively, in the case of ultrasound, the returned signal 194 may be the reflection of the injected sound waves off or some or all of the subject being monitored.

The returned signal 194 is provided to a signal-to-noise ratio (SNR) calculator 178 and to a signal analysis selector 184.

The SNR calculator 178 analyzes the returned signal 194 to determine a signal to noise ratio for the returned signal 194. It should be understood that, while not depicted, additional signal processing components, such as filters and an AD converter may be disposed between the signal transducer 186 and the SNR calculator 178, such that the returned signal 194 received by the SNR calculator 178 is an improved quality version of the raw returned signal 194 collected by the signal transducer 186.

The signal analysis selector 184 also receives the returned signal 194. The signal analysis selector 184 processes the returned signal 194 in order to determine the proper signal analysis technique that should be used in order to obtain results of a desired quality. The signal analysis selector 184 may take into account, as will be described in further detail herein, the presently available signal processing techniques, as well as the quality of the result that may be obtained from each of the available signal processing techniques. The selected signal analysis technique from the signal analysis selector 184 is provided to the rest of the signal analysis components 188 for analyzing the quasi-periodic signal.

The $T_x$ power controller 180 receives both the computed SNR of the returned signal 194 from the SNR calculator 178 and also receives an indication of the selected signal analysis technique from the signal analysis selector 184. The $T_x$ power controller 180 uses the selected signal analysis technique to obtain an optimal SNR range for the returned signal 194 and the selected signal analysis technique. The optimal SNR ranges may be stored in an SNR range database 196 that is connected to the $T_x$ power controller 180. The SNR range database 196 may include a variety of SNR ranges, based upon the particular returned signal 194 being acquired and the various potential applicable signal analysis techniques. The SNR range database 196 may be organized in the form of a look up table of range values. The optimal SNR range identified in the SNR range database 196 may be determined based upon creating a range that optimizes signal analysis quality and portable power source life through reduced signal transducer transmission power.

The $T_x$ power controller 180 may compare the calculated SNR to the obtained optimal SNR range. If the calculated SNR from the SNR calculator 178 is lower than the optimal range, this is indicative that the transmission power of the signal transducer 186 is too low for the noise conditions of the subject. In this case, the $T_x$ power controller 180 produces a $T_x$ power control signal 182 to increase the power of the stimulus signal 192 produced by the signal transducer 186.

If the $T_x$ power controller 180 determines that the SNR calculated by the SNR calculator 178 is greater than the optimal SNR range, then the $T_x$ power controller 180 produces a $T_x$ power control signal 182 that is sent to the signal transducer 186 to decrease the transmission power of the stimulus signal 192, such that the signal transducer 186 uses less power and promotes the life of the portable power source. If the $T_x$ power controller 180 determines that the calculated SNR is within the optimal SNR range, then the $T_x$ power controller 180 produces a $T_x$ power control signal 182 that maintains the current transmission power of the stimulus signal 192 produced by the signal transducer 186.

Figure 12:
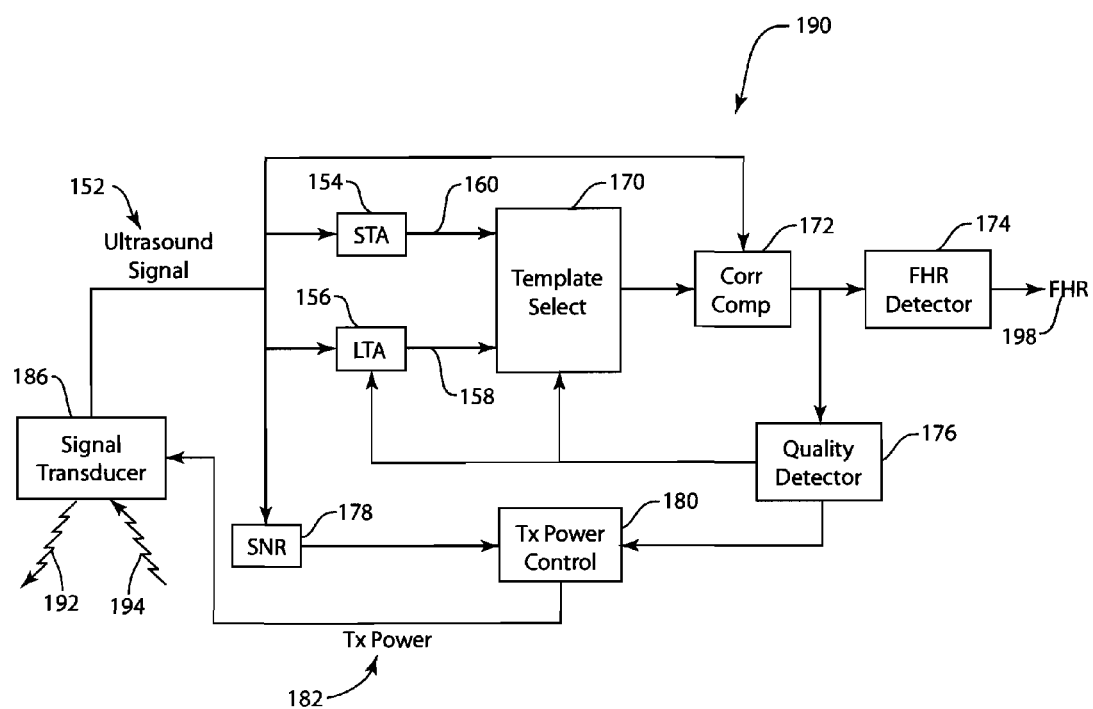
FIG. 12 depicts a device for controlling the transmission power of an ultrasound signal produced by an ultrasound signal generator used to monitor fetal heart rate.

FIG. 12 depicts an embodiment of an FHR detector 190. The FHR detector device incorporates elements from the disclosed FHR detector of FIG. 10 as well as the $T_x$ power control device disclosed in FIG. 11. In the FHR detector device 190, the signal transducer 186 is an ultrasound transducer that produces a stimulus signal 192 in the form of a sound wave that passes through the abdomen of the patient and reflects off of the fetus within. As the fetus' heart beats, the reflected sound waves that make up the returned signal 194 change in a quasi-periodic fashion. The returned ultrasound signal 152 is then provided to a variety of components for processing.

The returned ultrasound signal 152 is provided to an STA template creator 154 and an LTA template creator 156. The STA template creator 154 and the LTA template creator 156 work as described previously to create an STA template 160 and an LTA template 158 that are both provided to the template selector 170. The template selected by the template selector 170 is provided to a correlation computer 172, which is also provided with the returned ultrasound signal 152. The correlation computer 172 cross correlates the selected template with the returned ultrasound signal 152 to produce a correlation signal.

The correlation signal is provided to a FHR detector 174 that measures the instantaneous fetal heart rate 198 by measuring the instantaneous period between each of the correlation peaks in the correlation signal.

The correlation signals are also provided to a quality detector 176. The quality detector 176 determines the quality of the correlation signal in one of the manners as previously described and provides a control signal to the template selector 170 and the LTA template creator 156 such that the template selector 170 is able to select between the STA template and the LTA template and, when the LTA template is determined to produce inferior results, the control signal from the quality detector 176 to the LTA template creator 156 initiates the LTA template creator 156 to create a new LTA template.

The returned ultrasound signal 152 is also provided to a signal-to-noise ratio calculator 178. The signal-to-noise ratio calculator 178 calculates the signal-to-noise ratio of the returned ultrasound signal 152. This signal-to-noise ratio is provided to a $T_x$ power control 180.

The $T_x$ power control 180 also receives the quality indication from the quality detector 176. Based upon the received quality indication from the quality detector 176, the $T_x$ power control 180 can determine which signal analysis technique is being selected by the template selector 170 for use by the correlation computer 172 in determining the instantaneous fetal heart rate 198. After receiving this indication, the $T_x$ power control 180 can obtain a predetermined optimal signal-to-noise range values. These range values may be stored in a data storage device (not depicted) for convenient retrieval by the $T_x$ power control 180.

Figure 14:
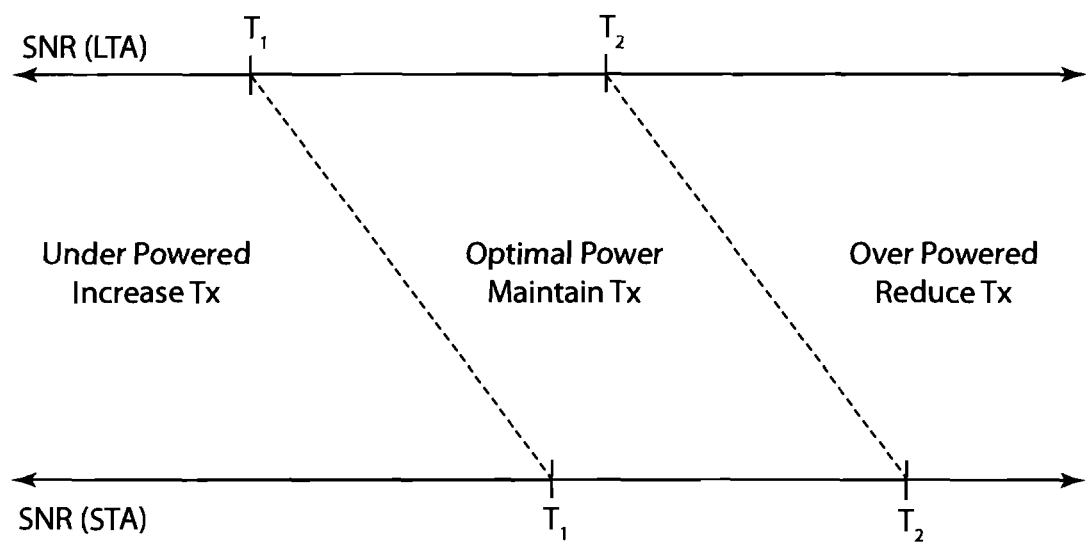
FIG. 14 is a graph depicting the optimal signal-to-noise ratio range for a first signal analysis technique and a second signal analysis technique.

FIG. 14 is a graph showing a comparison of exemplary optimal SNR range values that may be stored in the data storage device and used by the $T_x$ power control 180. In the graph of FIG. 14, two SNR ranges are depicted. The top of the graph shows the SNR range required for LTA. The bottom of the graph shows the SNR range required for STA. The overall SNR range for each of LTA and STA can be divided by the required transmission power control for each SNR level. The predefined optimal transmission power range (defined as a balance between SNR quality and power usage) may be defined by a pair of SNR values ($T_1$ and $T_2$) that represent the lower and upper SNR bounds of the optimal transmission power range. As shown in FIG. 14, generally a greater amount of transmission power is required to produce the same SNR quality of results (and corresponding optimal transmission power) using STA as compared to using LTA. Therefore, the SNR values for $T_1$ and $T_2$ for the optimal STA transmission power range are generally greater than the LTA SNR values for $T_1$ and $T_2$.

The $T_x$ power control 180 depicted in FIG. 12 operates as shown in FIG. 14 such that if the SNR of the returned ultrasound signal is less than the value of $T_1$ for the selected analysis technique, then the $T_x$ power control 180 produces a $T_x$ power control signal to increase the transmission power of the signal transducer 186. Similarly, if the calculated SNR is greater than the SNR range value $T_2$, then the signal transducer 186 is overpowered and is operating inefficiently by using more power than is required to perform the desired signal analysis. Therefore, the $T_x$ power control 180 produces a $T_x$ power control signal 182 to reduce the transmission power of the signal transducer 186. If the SNR is between the values $T_1$ and $T_2$, then it is determined that the signal transducer 186 is operating at the optimal transmission power and therefore the $T_x$ power control 180 produces a $T_x$ power control signal 182 to maintain the transmission power of the signal transducer 186.

It should be noted that a variety of optimal transmission power ranges, defined by the SNR pair $T_1$ and $T_2$ may be stored for use with the FHR detector device. The predetermined optimal transmission power ranges may be determined and stored for a variety of analysis techniques including LTA and STA techniques, but may also include variations based upon the signal processing being performed on the returned signal or the physical or physiological properties of the subject being monitored. It is to be understood that while no numerical values for $T_1$ and $T_2$ are herein provided, the values of $T_1$ and $T_2$ will generally be dependent upon the specific LTA and STA algorithms used, as well as clinical conditions, as will be discussed in further detail below. In an exemplary embodiment, the SNR values ($T_1$ and $T_2$) for the LTA optimal transmission power range is between 18 and 36% lower than the SNR values ($T_1$ and $T_2$) for the STA optimal transmission power range. In another exemplary embodiment, the LTA SNR values are 25% lower than the STA SNR values. In a further exemplary embodiment, the LTA SNR values are more than 36% lower than the STA SNR values.

Some factors have been identified in the clinical setting that reduce the SNR of the returned signal, thus reducing the quality of the FHR analysis as well as requiring increased transmission power by the transducer. One of these such factors is maternal obesity. The additional abdominal tissue of the obese mother present a barrier to the transmission of the ultrasound signal, thus reducing the SNR of the returned signal. Therefore, improved transmission power control based upon the SNR of the returned signal and the selected analysis techniques allows for a device and method that provide improved FHR detection when the mother is obese. This also provides a more robust equipment that is able to accurately measure FHR, regardless of the patient's body fat.

The SNR of the returned signal is also reduced based upon the displacement of the fetal heart relative to the ultrasound transducer placed on the mother's abdomen due to movement by the mother or the fetus. As the SNR of the returned signal changes with movement by the fetus and/or the mother, the improved dynamic control of the transmission power (and the resulting SNR of the returned signal) provides a device and method in which the fetal heart rate may be monitored more accurately during periods in which the mother or the fetus is ambulatory, or during labor.

Other techniques or conditions have been identified in the clinical setting that also increase the SNR of the returned signal. These conditions include the quality and sensitivity of the ultrasound receiver. Additionally, ultrasound emitters with improved focusing of the ultrasound beam, and/or orientation of the ultrasound crystals produce improved direction of the ultrasound beam, resulting in a higher quality returned signal. It is understood that the presently disclosed device and method, when combined with one or more of these conditions or techniques, may further reduce the transmission power required by the ultrasound transducer.

Figure 13:
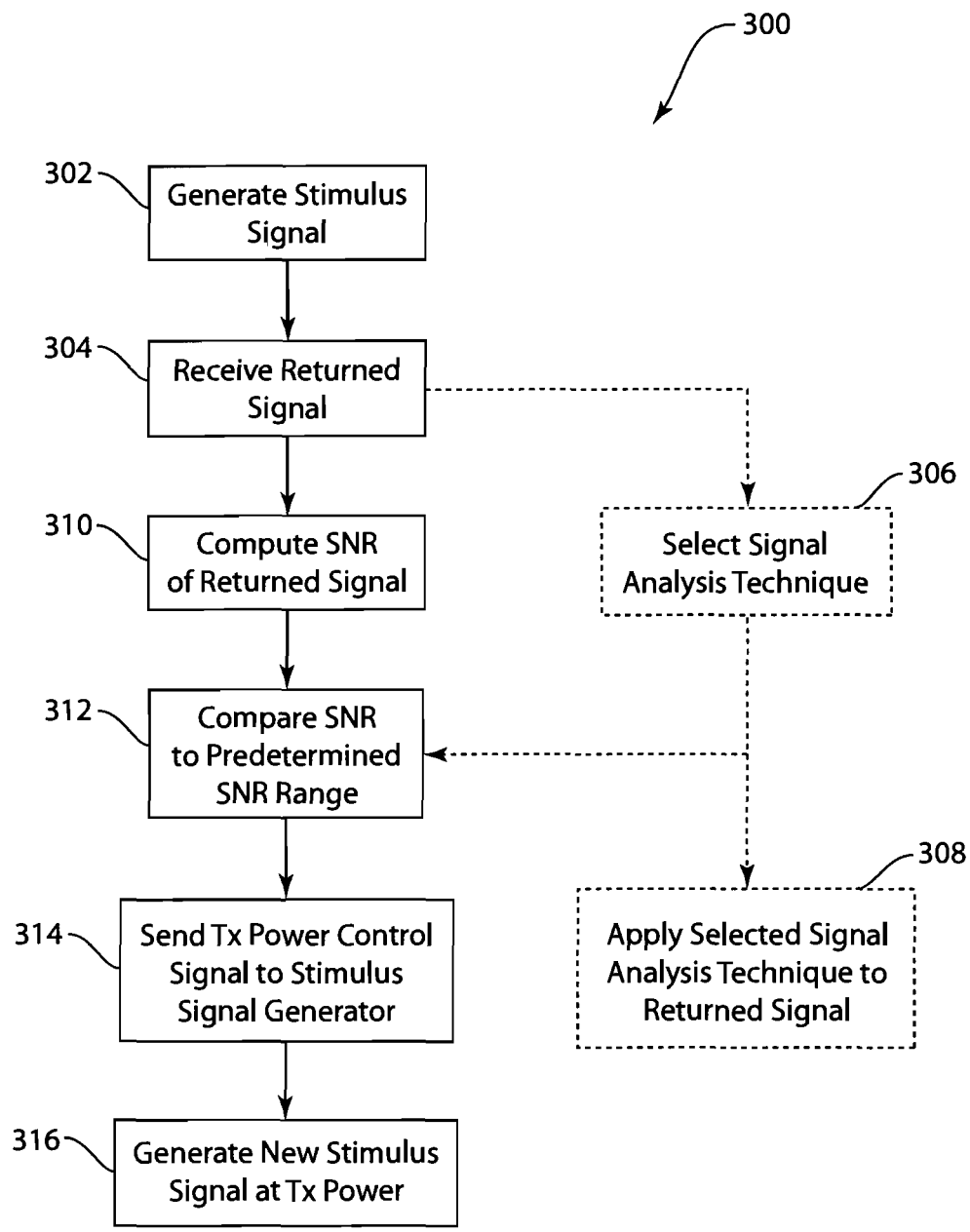
FIG. 13 is a flow chart depicting an embodiment of the steps of a method for controlling the transmission power of a stimulus signal.

FIG. 13 is a flow chart depicting a method 300 of controlling the transmission power of a stimulus signal.

At step 302, a stimulus signal is generated. As previously described, the stimulus signal may be of a variety of types of stimulus signals, and in one embodiment, may be an ultrasound signal produced by an ultrasound generator and transducer.

Next, at step 304, the returned signal is received. In response to the stimulus signal, the subject being monitored will produce, or reflect, a returned signal. This returned signal is collected and monitored.

Next, at step 310, the signal-to-noise ratio (SNR) of the returned signal is computed. This may be performed by a dedicated circuit, or may be performed by an algorithm or program stored on a computer readable medium that is executed by a computer processor.

Then, the computed SNR is compared to a predetermined SNR range at step 312. The predetermined SNR range may be stored remotely on a data storage medium and may represent an optimal SNR range for the analysis of the returned signal.

Next, at step 314, $T_x$ power control signal is sent to the stimulus signal generator. The $T_x$ power control signal controls the stimulus signal generator to operate at a new value of transmission power and at step 316, a new stimulus signal is generated at the transmission power indicated by the $T_x$ power control signal.

Alternative embodiments of the method 300 may also include additional steps as well. After the returned signal has been received at step 304, the returned signal may be used in step 306 in order to select the proper signal analysis technique to be used to process the returned signal. The signal analysis technique may be selected in step 306 based upon the desired information to be obtained from the returned signal, as well as the quality of the returned signal, or the quality of the results that may be obtained from the returned signal based upon the differences between the potential signal analysis techniques from which one is selected. The selected signal analysis technique in 306 may also be used in step 312 in order to select a predetermined SNR range for comparison to the computed SNR. Additionally, after a signal analysis technique has been selected in step 306, in step 308, the selected signal analysis technique may be applied to the returned signal in order to process the returned signal to obtain the desired information.

The additional control of the transmission power of an active transducer as achieved by the disclosed embodiments of the system and method presents numerous advantages, specifically in the field of fetal heart rate monitoring. First, the SNR of the return signal changes as the position of the fetus within the mother changes with respect to the transducer. Thus, the control of the transmission power can be achieved with respect to the position of the fetus and the corresponding change in the SNR of the return signal. Lower transmission power is required by the transducer when the fetus is in a preferred position, while transmission power is increased during times in which the fetus is in an undesirable position. Also, during period of LTA fetal heart rate analysis, the same transmission power produces a higher quality of an input signal resulting in a higher quality of FHR analysis than that is achieved at the same transmission power using STA. This increased quality provides an option to a clinician, or a controller within the monitoring device, in that the increased FHR quality during LTA may be used to improve the quality of results, or may conversely may be used to decrease the required transmission power of the transducer, while still providing FHR analysis of a quality that is equivalent to or higher than that which is achieved using STA techniques and a higher transmission power.

Some of the embodiments of the system and method as disclosed herein may be performed and/or implemented through solely the use of a computer. Components or steps of embodiments may be performed by a series of dedicated use computers, by computer programs or computer program modules as specifically designed for use on a general purpose computer to carry out the steps and functions as disclosed herein. In these computer implemented embodiments, the technical effect of the presently disclosed system and method is to provide a more accurate analysis of quasi-periodic signals, resulting in improved transmission power control of active transducer.

As noted previously, the present description has focused on specifically the quasi-periodic signal of the Doppler shift of an ultrasound signal due to a fetal heart beat. It should be likewise be understood that the system and method as disclosed herein may likewise be also used in other types of biosignal monitoring applications, such as ECG or EEG, or even in non-biological applications, such as measuring the angular velocity of a piece of rotating machinery.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A device for controlling the transmission power of an ultrasound signal produced by an ultrasound transducer used to monitor fetal heart rate (FHR), the device comprising:
    a signal to noise ratio (SNR) calculator that receives a returned signal from an ultrasound transducer, the returned signal having passed through the body of a patient and computes an SNR for the returned signal;
    a short term analysis (STA) template generator that receives the returned signal and creates an STA template from a short duration portion of the returned signal;
    a long term analysis (LTA) template generator that receives the returned signal and creates an LTA template for which a number of correlation peaks is maximized by iteratively correlating successive templates over a long duration portion of the returned signal;
    a template selector that selects between the LTA template and the STA template, and produces a control signal indicative of the selected template;
    an FHR detector that cross correlates the selected template with the returned signal to determine an instantaneous fetal heart rate; and
    a transmission power controller that receives the signal indicative of the selected template, selects a predefined optimal SNR range for the selected template, compares the computed SNR for the returned signal to the selected predefined optimal SNR range, and produces a control signal which is sent to the ultrasound transducer to modify the transmission power of the ultrasound transducer thereby modifying the SNR of the returned signal.

2. The device of claim 1, wherein:
    if the computed SNR is lower than the predefined optimal SNR range, the control signal is sent to the ultrasound transducer to increase the transmission power;
    if the computed SNR is higher than the predefined optimal SNR range, the control signal is sent to the ultrasound transducer to decrease the transmission power; and
    if the computed SNR is within the predefined optimal SNR range, the control signal is sent to the ultrasound transducer to maintain the current transmission power.

3. The device of claim 2, wherein when the transmission power controller receives the signal indicative of the LTA template, the transmission power controller selects a first optimal SNR range and when the transmission power controller receives the signal indicative of the STA template the transmission power controller selects a second optimal SNR range, wherein the first optimal SNR range is lower than the second optimal SNR range.

4. The device of claim 1 wherein the optimal SNR range for the LTA template is at least 18% lower than the optimal SNR range for the STA template.

5. The device of claim 4 wherein the optimal SNR range for the LTA template is between 18% and 36% lower than the optimal SNR range for the STA template.

6. The device of claim 1 wherein,
    the optimal SNR range for the selected template is defined by a lower bound value and an upper bound value, and
    if the SNR for the returned signal is less than the lower bound value, the control signal produced by the transmission power controller increases the transmission power of the ultrasound transducer,
    if the SNR for the returned signal is greater than the upper bound, the control signal produced by the transmission power controller reduces the transmission power of the ultrasound transducer, and
    if the SNR for the returned signal is between the lower bound value and the upper bound value, the control signal produced by the transmission power controller maintains the transmission power of the ultrasound transducer.

7. The device of claim 1, wherein the LTA template generator:
    cross correlates a first template with a long duration portion of the returned signal to create a first correlation signal;
    counts peaks in the first correlation signal greater than a predetermined threshold;
    selects portions of the returned signal that correspond to the counted peaks and averages the selected portions to create a second template; and
    repeats cross correlating to create correlation signals, counting peaks in the correlation signals, selecting portions that correspond to the counted peaks, and averaging the selected portions in order to maximize the counted peaks; and
    selects a template as the LTA template that maximizes the counted peaks.

8. The device of claim 7, wherein the short duration portion of the returned signal is less than or equal to two seconds.

9. The device of claim 7, wherein the long duration portion of the returned signal is greater than or equal to twelve seconds.

10. The device of claim 7, wherein the long duration portion of the returned signal is at least ten times longer than the short duration portion of the returned signal.

11. The device of claim 7, further comprising a quality detector that compares a first FHR determined using the LTA template to a second FHR determined using the STA template and produces an indication of which of the LTA template or STA template produces a higher quality determination of FHR.

12. A method of operating an ultrasound signal generator, the method comprising:
    generating a stimulus signal with the ultrasounds signal generator at a transmission power;
    receiving a returned signal in response to the stimulus signal;
    creating a short term analysis (STA) template from a short duration portion of the returned signal;
    cross correlating a first template with a long duration portion of the returned signal to create a first correlation signal;
    counting peaks in the first correlation signal greater than a predetermined threshold;
    selecting portions of the long duration portion of the returned signal that correspond to the counted peaks;

averaging the selected portions to create a second template;
repeating cross correlating to create correlation signals, counting peaks in the correlation signals, selecting portions that correspond to the counted peaks, and averaging the selected portions in order to maximize the counted peaks;
selecting an LTA template that maximizes the counted peaks;
deriving an instantaneous fetal heart rate from the returned signal using one of the STA template or the LTA template;
computing a signal to noise ratio (SNR) of the returned signal;
selecting a predetermined optimal SNR range based upon whether the STA template or LTA template was used to derive the instantaneous fetal heart rate;
comparing the SNR to the predetermined optimal SNR range;
controlling the transmission power to maintain the SNR within the predetermined optimal SNR range.

13. The method of claim 12, wherein the predetermined optimal SNR range associated with the LTA template is lower than the predetermined optimal SNR range associated with the STA template.

14. The method of claim 13, wherein the predetermined optimal SNR range associated with the LTA template is at least 18% lower than the predetermined optimal SNR range associated with the STA template.

15. The method of claim 12, further comprising:
deriving instantaneous fetal heart rates from the returned signal using both the STA template and the LTA template;
comparing the instantaneous fetal heart rate derived using the STA template to the instantaneous fetal heart rate derived using the LTA template;
selecting between the STA template and the LTA template based upon the template that produced a higher quality measurement of instantaneous fetal heart rate.

16. The method of claim 12, wherein the short duration portion of the returned signal is less than or equal to two seconds.

17. The method of claim 12, wherein the long duration portion of the returned signal is greater than or equal to twelve seconds.

18. The method of claim 12, wherein the long duration portion of the returned signal is at least ten times longer than the short duration portion of the returned signal.

* * * * *